US011918658B2

(12) United States Patent
Godfrin et al.

(10) Patent No.: US 11,918,658 B2
(45) Date of Patent: Mar. 5, 2024

(54) HYDROGELS AND RELATED COMPOSITIONS AND METHODS

(71) Applicant: Massachusetts Institute of Technology, Cambridge, MA (US)

(72) Inventors: Paul Douglas Godfrin, Boston, MA (US); Patrick S. Doyle, Sudbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 955 days.

(21) Appl. No.: 16/604,322

(22) PCT Filed: Apr. 12, 2018

(86) PCT No.: PCT/US2018/027297
§ 371 (c)(1),
(2) Date: Oct. 10, 2019

(87) PCT Pub. No.: WO2018/191494
PCT Pub. Date: Oct. 18, 2018

(65) Prior Publication Data
US 2022/0331444 A1 Oct. 20, 2022

Related U.S. Application Data

(60) Provisional application No. 62/484,708, filed on Apr. 12, 2017.

(51) Int. Cl.
*A61K 47/69* (2017.01)
*A61K 31/216* (2006.01)
*A61K 47/60* (2017.01)

(52) U.S. Cl.
CPC ........ *A61K 47/6903* (2017.08); *A61K 31/216* (2013.01); *A61K 47/60* (2017.08); *A61K 47/6907* (2017.08)

(58) Field of Classification Search
CPC .. A61K 47/60; A61K 47/6903; A61K 31/216; A61K 47/6907
See application file for complete search history.

(56) References Cited

U.S. PATENT DOCUMENTS

2011/0033540 A1* 2/2011 Daniloff .................. A61L 27/20
424/484
2011/0183001 A1* 7/2011 Rosson ............... A61L 27/3687
435/395

OTHER PUBLICATIONS

Bromberg, "Intelligent hydrogels for the oral delivery of chemotherapeutics", Expert Opin. Drug Deliv., 2(6), 1003-1013, 2005. (Year: 2005).*
Badruddoza et al., Core-Shell Composite Hydrogels for Controlled Nanocrystal Formation and Release of Hydrophobic Active Pharmaceutical Ingredients. Adv Healthc Mater. Aug. 2016;5(15):1960-8. doi: 10.1002/adhm.201600266. Epub Jun. 1, 2016.
Chookajorn et al., Design of stable nanocrystalline alloys. Science. Aug. 24, 2012;337(6097):951-4. doi: 10.1126/science.1224737.

(Continued)

*Primary Examiner* — Jianfeng Song
(74) *Attorney, Agent, or Firm* — Wolf, Greenfield & Sacks, P.C.

(57) ABSTRACT

Embodiments described herein relate to hydrogels, and in particular, hydrogels for crystal formation, and related compositions and methods.

17 Claims, 16 Drawing Sheets

(56) References Cited

OTHER PUBLICATIONS

Tan et al., Highly stretchable and resilient hydrogels from the copolymerization of acrylamide and a polymerizable macromolecular surfactant. Polym Chem. 2013;4:5570-5576.
PCT/US2018/027297, Jul. 2, 2018, International Search Report and Written Opinion.
PCT/US2018/027297, Oct. 24, 2019, International Preliminary Report on Patentability.
Godfrin et al., Photopolymerized Micelle-Laden Hydrogels Can Simultaneously Form and Encapsulate Nanocrystals to Improve Drug Substance Solubility and Expedite Drug Product Design. Small. Feb. 2019;15(6):e1803372. doi:10.1002/smll.201803372. Epub Jan. 15, 2019.

\* cited by examiner

_US 11,918,658 B2_

HYDROGELS AND RELATED COMPOSITIONS AND METHODS

RELATED APPLICATIONS

This application is a national stage filing under 35 U.S.C. § 371 of International Patent Application Serial No. PCT/US2018/027297, filed Apr. 12, 2018, entitled "HYDROGELS AND RELATED COMPOSITIONS AND METHODS", which claims priority under 35 U.S.C. § 119(e) to U.S. provisional application No. 62/484,708, filed Apr. 12, 2017, the contents of which is incorporated herein by reference in its entirety.

FIELD OF THE INVENTION

Embodiments described herein relate to hydrogels, and in particular, hydrogels for crystal formation, and related compositions and methods.

BACKGROUND OF THE INVENTION

As a result of high-throughput methodologies for drug discovery, a significant portion of new drug substances are hydrophobic in nature. Hydrophobic active pharmaceutical ingredients (APIs) constitute roughly 40% of all small molecules that are commercially available or under development in pipelines. While hydrophobic APIs have received significant attention for their therapeutic activity, the limited solubility of these materials in aqueous environments limits their effectiveness as drug products. In particular, these drugs tend to have slow release rates and poor uptake. Efforts have been made to enhance uptake of hydrophobic APIs by reducing their crystal size. The lower limit for the size of crystals generated using top down approaches, however, is limited to roughly 200-300 nm.

Hydrogels comprise water (or other aqueous solvent) embedded in a cross-linked polymeric network that provides mechanical strength.

Surfactant present in a solution often arranges into micelles. The surfactant molecules may comprise a hydrophobic region and a hydrophilic region. When the surfactant is arranged to form a micelle, generally, the micelle defines a core in an internal region. Generally, the surfactants are arranged such that the hydrophobic region faces toward the core, while the hydrophilic region faces away from the core.

Accordingly, methods and compositions whose applications could include improving performance of hydrophobic APIs are desired within the field.

SUMMARY OF THE INVENTION

Various compositions and methods are provided.

In some embodiments, the composition comprises a hydrogel. The hydrogel may comprise a cross-linked polymeric matrix comprising a cross-linked species and a cross-linking agent. Thy hydrogel may further comprise a plurality of micelles bonded to the cross-linked polymeric matrix.

In some embodiments, the composition comprises a plurality of substantially stable nanocrystals, wherein the stable nanocrystals have an average size of between 5 nm and 200 nm, or of between 30 nm and 50 nm.

In some embodiments, methods of forming a hydrogel are provided. The method may comprise reacting a precursor comprising an aqueous solvent, a polymer precursor species, a cross-linking agent, and a surfactant species to produce a hydrogel comprising a cross-linked polymeric matrix, wherein a plurality of micelles comprising the surfactant species are bonded to the cross-linked polymeric matrix.

In some embodiments, methods of forming a plurality of nanocrystals are provided. The method may comprise introducing a crystal seeding material to a hydrogel, the hydrogel comprising a cross-linked polymeric matrix, wherein a plurality of micelles comprising the surfactant species are bonded to the cross-linked polymeric matrix; and forming a plurality of nanocrystals within cores of the plurality of micelles.

Figure 1A:
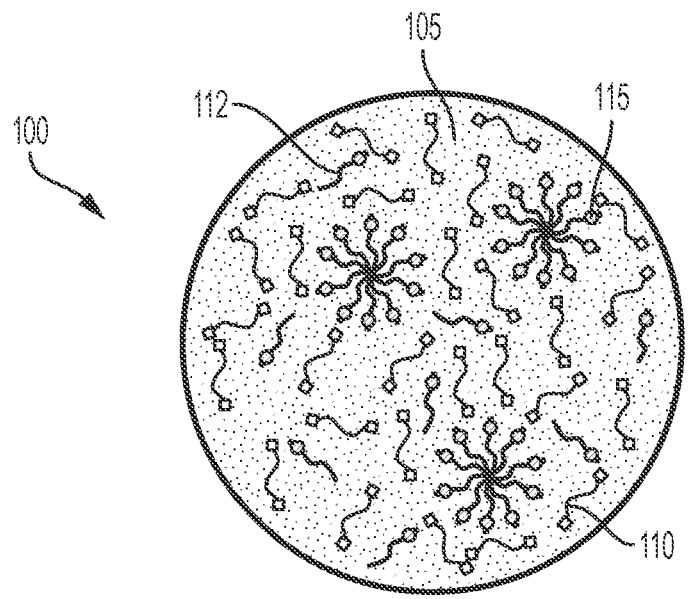
FIG. 1A shows a composition comprising hydrogel precursor, according to one or more embodiments.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Embodiments described herein relate to hydrogels, including hydrogels that may facilitate crystal formation, and related compositions and methods.

According to one or more embodiments, compositions comprising hydrogels e.g., micelle-laden hydrogels) are generally described. In some embodiments, compositions comprising crystals (e.g., nanocrystals) are generally described. According to one or more embodiments, methods for synthesizing hydrogels and for synthesizing crystals within the hydrogels are generally described.

According to one or more embodiments, the hydrogel comprises a cross-linked polymeric matrix. The hydrogel may further comprise an aqueous solvent (e.g., water). The cross-linked polymeric network may provide mechanical strength to the hydrogel. A plurality of micelles may be bonded to the cross-linked polymeric matrix. For convenience, hydrogels comprising a plurality of micelles bonded to the cross-linked polymeric matrix are often referred to, herein, as "micelle-laden hydrogels." The micelles incorporated into the network may produce domains (e.g., nanodomains within Which a crystallizing seeding material will nucleate and grow). The micelles may vary in structure to alter the size of the crystallization domains and the chemical environment to crystallize a wide range of materials.

The matrix may comprise a cross-linked species and a cross-linking agent. The cross-linked species may be a polymeric species (e.g., polyethylene (glycol) diacrylate ("PEGDA")). The polymeric species may be cross-linked by a suitable cross-linking agent. The cross-linking agent may be a photoinitiator (e.g., an alkylphenone). In embodiments where the cross-linking is a photoinitiator, a photochemical process (e.g., exposure to UV light) may be used to implement formation of the matrix; however, other processes may also be used. Examples of the cross-linked (i.e. polymer) species include, without limitation: poly(ethylene glycol) and its derivatives, cellulose and its derivatives, poly(propylene glycol) and its derivatives, polylactide and its derivatives, poly(glycolic acid) and its derivatives, poly(propylene fumarate) and its derivatives, polycaprolactone and its derivatives, polyhydroxybutyrate and its derivatives, polyacrylates and derivatives, poly(vinylpyrrolidone) and derivatives, and poly(ethylenimine) and its derivatives. In some embodiments, the polymer species comprises PEGDA. Examples of photoinitiators that may serve as the cross-linker species include, without limitation: alkylphenones, acetophenones, benzoin ethers, acyl phosphine oxides, and benzophenones.

The plurality of micelles may comprise surfactant (e.g., a non-ionic surfactant). The surfactant forming the micelles may be bonded to the polymeric matrix. The surfactant molecules may comprise a hydrophobic region and a hydrophilic region. When the surfactant is arranged to form a micelle, generally, the micelle defines a core in an internal region. Generally, the surfactants are arranged such that the hydrophobic region faces toward the core, while the hydrophilic region faces away from the core. In some embodiments, the hydrophilic region of the surfactant comprises poly(ethylene glycol). In some embodiments the hydrophobic region comprises polyethylene. In some embodiments, the hydrophobic region of the surfactant comprises poly(propylene glycol).

In some embodiments, integrating micelle templated hydrophobic domains into hydrogel matrices involves the surfactants being capable of chemically bonding to the polymer backbone. In some embodiments the surfactant may be modified to include a functional group. Functionalizing the surfactant may facilitate its bonding to the matrix. In some embodiments, the surfactant may comprise a functional group positioned in the hydrophilic region of the surfactant. In some embodiments, the functional group of the surfactant is bonded to the cross-linked species of the polymeric matrix. In this manner, the bonding of the plurality of micelles to the matrix may be accomplished. The functional group may be bonded to the cross-linked species during, for example, a photochemical reaction. The functional group by which the surfactant is modified may be chosen so that it will bond to the polymeric matrix. For example, in embodiments comprising a PEGDA network, the surfactant may be modified to include an acrylate group that chemically bonds to the PEG-DA network during the cross-linking reaction.

In some embodiments, the functional group is an acrylate group. In some embodiments, the functional group may be selected from, for example, acrylates, alkenes, alkynes, and nitriles. Additional species from which the functional group may be selected includes hydroxyls, alcohols, epoxies, amines, thiols, and sulfides. Other species may also serve as the functional group. According to one or more embodiments, functionalized surfactants (e.g., surfactants modified to comprise an acrylate or other group) may be integrated into hydrogel scaffolds to serve as domains for the crystallization of seed material (e.g., hydrophobic APIs).

In some embodiments, the composition comprising the hydrogel may further comprise a crystal seeding material. The seeding material may be introduced to the hydrogel as part of a solution. Crystal seeding material may be positioned within the plurality of micelle cores. The crystal seeding material may be hydrophobic. In some embodiments, the micelle cores define hydrophobic domains configured to facilitate crystallization of a hydrophobic crystal seeding material. Hydrophobic crystal seeding material positioned in the hydrophobic domains may form crystals with desired properties. In some embodiments, the crystal seeding material comprises an active pharmaceutical ingredient ("API"). The API may be hydrophobic.

In some embodiments, the composition may further comprise stable crystals positioned within the micelle cores (e.g., hydrophobic domains). The stable crystals may grow from the crystal seeding material. Methods of forming the crystals are discussed further, herein.

Without being bound to a particular theory, it is believed that the carbon (alkyl) chain length of the hydrophobic region of the surfactant may affect how reliably crystallization may be induced. In some embodiments, the hydrophobic region has a particular carbon chain length. In some embodiments the carbon (alkyl) chain length of the hydrophobic region is at least 10, at least 15, at least 18, at least 20, at least 25, or at least 40. In some embodiments the hydrophobic chain length is equal to or less than 50, 40, 30, 20, 18, or 15. Combinations of the above values are possible. Other values are also possible.

Depending on the application, the composition of the hydrogel and surfactant can be tuned to produce a wide range of crystal size distributions. The size of the crystals formed with the micelle core may be related to the size of the micelle core itself. In some embodiments, surfactant species may be selected to provide micelle cores having an average diameter of a particular value or within a certain range of values, in order to produce crystals at a particular average diameter or within a certain range of diameters. Without being bound to a particular theory it is believed that crystal size correlates roughly with the hydrodynamic diameter of the micelle prior to integration into a hydrogel. The hydrodynamic diameter of the micelles may set an upper limit for nanocrystal size, reflecting the fact that the internal hydrophobic core is only a portion of the total volume of the micelle.

In some embodiments, the micelle cores may have an average diameter of from 5 nm to 50 nm. In some embodiments, the micelle cores may have an average diameter at least 5 nm, 20 nm, 50 nm, 100 nm, or 500 nm. In some embodiments the micelle cores may have an average diameter of less than or equal to 1000 nm, 500 nm, 100, 50 nm, or 20 nm, Ranges of the above values are also possible (e.g., from 5 nm to 50 nm). Other values are also possible, depending on the application. In some embodiments, crystals having a particular size may be formed. The crystals may be nanocrystals (crystals having a diameter in the nanoscale). In some embodiments, the crystals formed (e.g., stable crystals) have an average diameter of at least 5 nm, 20 nm, 30 nm, 50 nm, 100 nm, or 200 nm. In some embodiments, the crystals formed have an average diameter of less than or equal to 500 nm, 200 nm, 100, nm, 50 nm, 30 nm, or 20 nm. Combinations of the above are also possible (e.g., crystals having an average diameter of from 5 nm to 200 nm, or from 30 nm to 50 nm).

In some embodiments, the micelle laden hydrogel may be formulated to yield high loading of crystals with minimal surfactant content. The critical micelle concentration of the surfactants may be selected to provide a small barrier to the formation of micelles and therefore of nanoscale hydrophobic domains. Given that pores within the hydrogel mesh may serve as nucleation centers, the surfactant content of the hydrogel may be formulated to provide a critical density of micelle domains sufficient to drive crystallization to preferentially occur within these hydrophobic domains and yield an appreciable content of crystals. The amount of surfactant may be selected to avoid high surfactant concentrations in which spherical micelles may transition to larger lengthscale structures, such as vesicles, sheets, or worm like micelles, or self-associate into ordered cubic phases causing gelation (causing solution processing to be more difficult). Surfactant may spontaneously form micelles when present at a concentration above the critical micelle concentration (CMC). In some embodiments, the critical micelle concentration of the surfactants may be at least 1 µM, 5 µM, 10 µM, 50 µM, or 100 µM, and/or less than 200 µM, 100 µM, 50 µM, 10 µM, or 5 µM. Combinations of the above ranges are possible. Other values are also possible.

In the presence of surfactant, the hydrogel matrix may facilitate crystal formation both directly and indirectly by supporting micellar domains. The matrix may indirectly influence the hydrophobic domain size of the micelles if there is a size mismatch between the mesh and micelle diameter. If a micelle is larger than the mesh, then the internal domain may become constricted or become destabilized. Alternatively, a mesh much larger than a micelle may pull individual surfactant molecules too far apart to maintain a cohesive hydrophobic domain.

Turning to the FIGS., FIG. 1A shows a hydrogel precursor composition 100, according to one or more embodiments. The composition 100 is in a stage prior to the hydrogel forming, which may occur, for example, through application of UV light. In the embodiment shown, the hydrogel precursor composition 100 comprises solvent 105, polymer precursor 110, free surfactant 112, and surfactant arranged to form micelles 115. The composition 100 may also comprise a cross-linking agent (e.g., a photoinitiator) (not shown in FIG. 1A).

Figure 1B:
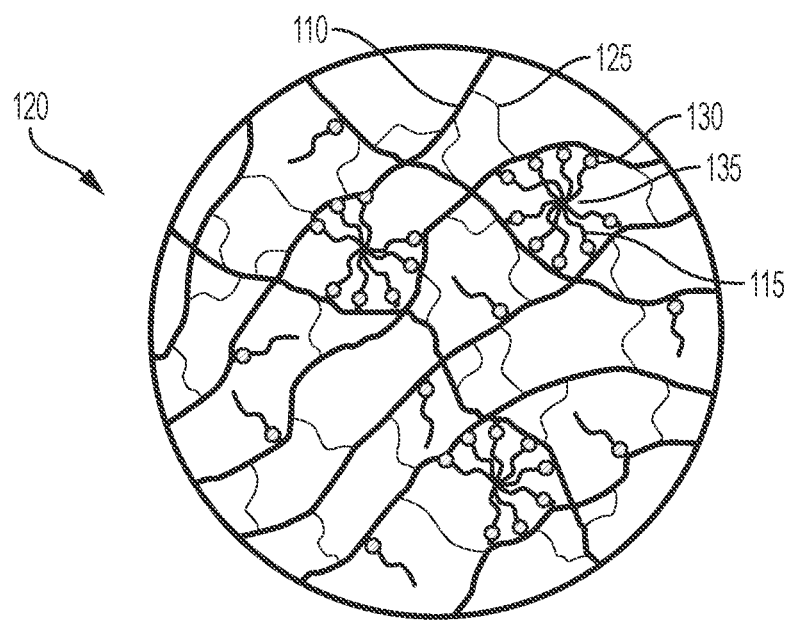
FIG. 1B shows a composition comprising a hydrogel, according to one or more embodiments.

FIG. 1B shows a hydrogel composition 120 according to one or more embodiments. The hydrogel composition comprises polymer 110 cross-linked by a cross-linking agent 125 to form a matrix. Micelles 115 are also bonded to the polymer 110. The surfactant forming the micelle 115 comprises a hydrophilic region 130 bonded to the polymer 110 and a hydrophobic region 135 defining a micelle core. In some embodiments, the hydrogel composition 120 may be formed by exposing the hydrogel precursor composition 100 to UV light.

Figure 1C:
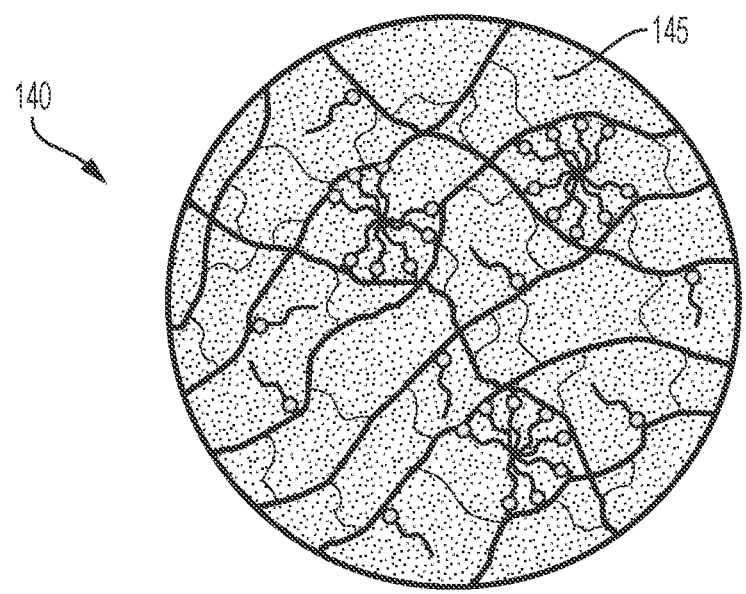
FIG. 1C shows a composition comprising a hydrogel and a crystal precursor solution, according to one or more embodiments.
Figure 1D:
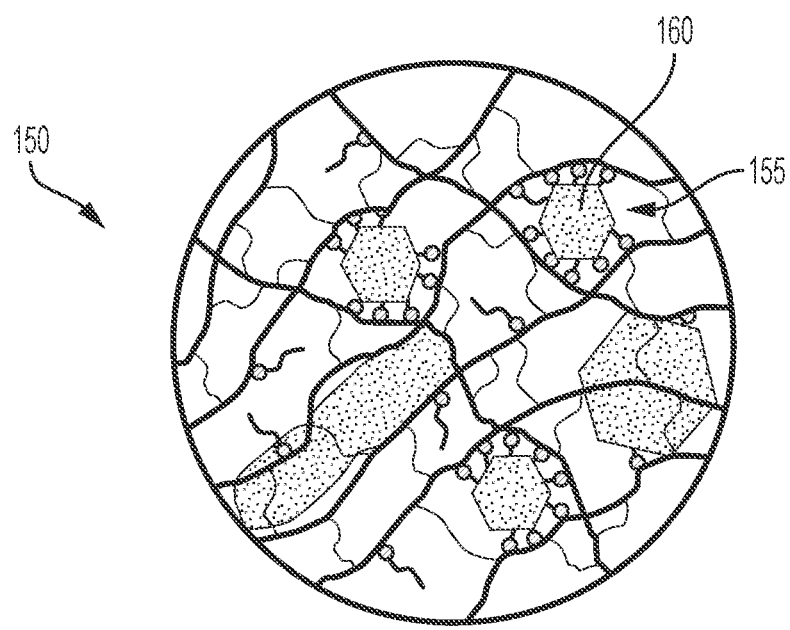
FIG. 1D shows a composition comprising a hydrogel and a plurality of crystals, according to one or more embodiments.
Figure 13:
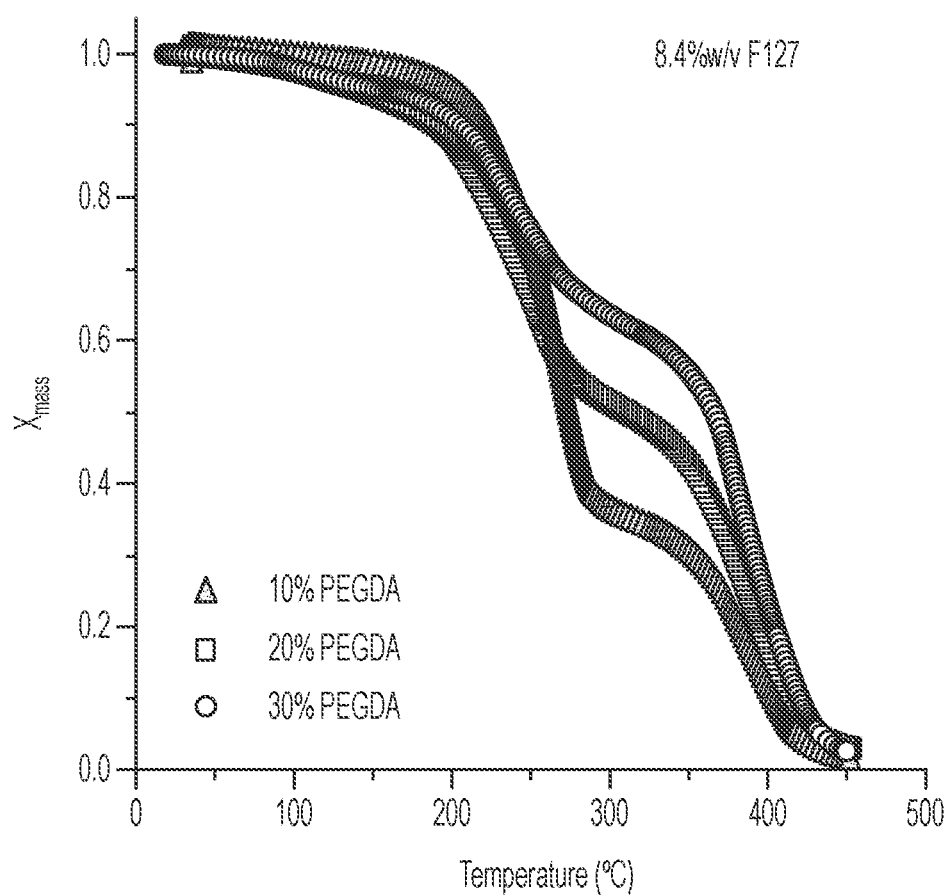
FIG. 13 shows the fraction of mass remaining as measured by TGA plotted as a function of temperature for hydrogels with varying amounts of PEGDA comprising the matrix. All hydrogels shown here are laden with F127 micelles and loaded with a solution of 450 mg/mL fenofibrate in ethyl acetate before drying, according to one or more embodiments.

FIG. 1C shows a composition 140 comprising a micelle-laden hydrogel, like that shown in FIG. 13, and a crystal precursor solution 145. The crystal precursor solution 145 comprises crystal seeding material (e.g., API material) that may be used to form crystals (e.g., nanocrystals). FIG. 1D shows a composition 150 comprising a plurality of crystals (e.g., nanocrystals) 160 formed in the micelle cores 155 of the micelle-laden hydrogel.

Methods for synthesizing the micelle-laden hydrogels described herein are also provided. In some embodiments, a method of forming the hydrogel may comprise reacting a precursor comprising a polymer precursor species (e.g. PEGDA), a cross-linking agent (e.g., a photoinitiator) and a surfactant species (e.g., a non-ionic surfactant).

In some embodiments, the reaction of the precursor to form the hydrogel occurs in a solution. In other embodiments, the reaction of the precursor to form the hydrogel occurs in a suspension or other mixture. The reaction may produce a hydrogel comprising a cross-linked polymeric matrix, with micelles comprising the surfactant species bonded to the matrix. Potential materials for use in the method are described above in relation to the composition.

The step of reacting may comprise exposing the precursor to actinic radiation (e.g., UV light). The wavelength may be any suitable wavelength (e.g., from 200 nm to 400 nm) depending on the species chosen. Other reaction mechanisms may also be used.

The method of forming a micelle-laden hydrogel may optionally further comprise washing the hydrogel to remove unreacted polymer precursor species, unreacted cross-linking agent, and unreacted surfactant species. The hydrogels produced by such a process may comprise properties and materials as discussed herein.

Methods for synthesizing the crystals (e.g., stable nanocrystals) described herein are also provided. In one set of embodiments, methods may involve introducing a crystal seeding material to a hydrogel as described herein. The hydrogel may comprise a cross-linked polymeric matrix, to which a plurality of micelles are bonded, as described elsewhere.

The method may further comprise forming crystals within cores of the micelles. The cores of the plurality of micelles may comprise hydrophobic domains for crystal nucleation. The internalization of nanocrystals within a hydrogel helps enhance the stability of the nanocrystal by preventing coalescence.

In some embodiments, the crystal seeding material is introduced to the hydrogel in the form of a seeding solution. The seeding solution may comprise a solvent and the seeding material as a solute. The synthesized micelle-laden hydrogels can be soaked in any solvent with a crystallizing substance (solute) of choice. The crystal seeding material may comprise an active pharmaceutical ingredient (e.g., a hydrophobic API).

The hydrogel may serve as a template for nanocrystal formation through solution processing. The step of forming a plurality of crystals may be performed by evaporating at least a portion of the solution to cause crystallization of the crystal seeding material. In some embodiments, solute crystal formation is induced by removing the solvent in an oven at an appropriate temperature for it to evaporate (a vacuum can be created to accelerate evaporation or reduce the temperature needed to evaporate). During evaporation, the solute concentration may exceed its solubility (supersaturates) and begins to crystallize preferentially in the nanodomains formed by the micelles bound in the hydrogel matrix.

The micelle size, which is determined, at least in part, by the chemistry of the surfactant, may dictate the size of the crystal. Therefore, nanocrystals may in some embodiments be produced in high yield with precisely controlled sizes. According to some embodiments, the average size of the formed nanocrystals may be controlled to within to within 20 nm, 10 nm, or 5 nm. Size may be controlled in part by controlling the size of the micelles of the hydrogel through, for example, surfactant selection.

According to one or more embodiments, compositions comprising substantially stable nanocrystals are provided. In some embodiments, the substantially stable nanocrystals have an average diameter of at least 5 nm, 20 nm, 30 nm, 50 nm, 100 nm, or 200 nm. In some embodiments, the substantially stable nanocrystals have an average diameter of less than or equal to 500 nm, 200 nm, 100, nm, 50 nm, 30 nm, or 20 nm. Combinations of the above are also possible (e.g., substantially stable nanocrystals having an average diameter of from 5 nm to 200 nm, or from 30 nm to 50 nm).

As used herein, a nanocrystal is substantially stable if the polymorph (i.e. crystal structure) and/or size of the nanocrystal, on average across the population of substantially stable nanocrystals, remains substantially unchanged while being stored under ambient conditions for at least one day. Ambient conditions for storage may correspond to roughly room temperature and typical indoor humidity (e.g., 22° C. and 40% relative humidity). The polymorph of a nanocrystal can be determined by measuring its X-ray powder diffraction (XRD) pattern. The polymorph of a plurality of nanocrystals is said to be substantially unchanged if the XRD pattern of the plurality of nanocrystals after a period of storage shows no new resolvable peaks at diffraction angles corresponding to other polymorphs of the material from which the nanocrystal is composed. A person of ordinary skill in the art would understand that a resolvable peak is one that can be distinguished from other peaks in the pattern, is reproducible, and has sufficient intensity to be distinguished from noise in the data. A person of ordinary skill would understand that a resolvable peak is not one that is caused by noise in the data or artifacts of the experiment. As a non-limiting example of a suitable XRD experiment for determining whether a nanocrystal is substantially stable, one could determine its polymorph before and after a period a storage by using a PANalytical XPert Pro XRD apparatus with a 4° aperture and 0.5° slit using a continuous scanning detector ranging from a 2θ angle of 4° to 40° with a scan rate of 1° min$^{-1}$. One could then compare the initial and final XRD patterns. In certain embodiments of substantially stable nanocrystals, the polymorph of the plurality of nanocrystals remains substantially unchanged after being stored under ambient conditions for at least two days, at least five days, at least 10 days, at least 30 days, or more after being formed, A non-limiting example of a plurality of nanocrystals maintaining a substantially unchanged polymorph even after being stored for 30 days under ambient conditions is related below.

According to one or more embodiments, the micelle-laden hydrogels allow the synthesized crystals to be protected in a chemical environment that significantly enhances the stability of nanocrystals to polymorphism and dissolution.

The substantially stable nanocrystals may comprise an active pharmaceutical ingredient. The nanocrystals may comprise a hydrophobic active pharmaceutical ingredient.

The composition may further comprise a plurality of micelles bonded to a cross-linked polymeric matrix, wherein the nanocrystals are positioned in the plurality of micelles.

According to some embodiments, applications of the compositions and methods described herein may include crystallization of active pharmaceutical ingredients as part of the manufacturing of drug products. Parameters of interest in such applications, include the polymorph of the crystals and crystal size which influence the release and stability. The methods and compositions disclosed herein, facilitate the control of these parameters. Furthermore, unlike other processes used during drug manufacturing, the methods disclosed herein are able to produce crystals in the nanoscale regime and/or do not require high energy input. In some embodiments, the hydrogels can serve as a delivery vehicle for enhanced uptake of hydrophobic drugs, as they simultaneously release drug with surfactant that increases the solubility in aqueous environments.

According to some embodiments, methods and compositions disclosed herein may aid in the manufacture of drugs comprising a hydrophobic active pharmaceutical ingredient (API). While hydrophobic APIs have received significant attention for their therapeutic activity, the limited solubility of these materials in aqueous environments, when manufactured according to methods previously known in the art, limits their effectiveness as drug products. In particular, these drugs manufactured according to previously known methods tend to have slow release rates and poor uptake. According to certain embodiments, methods and compositions disclosed herein may enhance hydrophobic API solubility by, for example, reducing the stable crystal size. The disclosed methods and compositions may aid in the formation of drug products with an optimal combination of high drug loading, long-term stability, and fast release. Disclosed micelle-laden hydrogels may serve as an effective framework to synthesize nanocrystals of hydrophobic APIs and enhance their release and solubility during delivery.

Having thus described several aspects of some embodiments of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the description and drawings are by way of example only.

The following examples are intended to illustrate certain embodiments of the present invention, but do not exemplify the full scope of the invention.

EXAMPLES

Non-Limiting Example 1

Example 1 describes further experimentation, embodiments, and non-limiting theories regarding the mechanisms and parameters guiding hydrogel and crystal formation. The materials and parameter values described in Example 1 are non-limiting and by way of example, only.

A hydrogel scaffold was synthesized that can produce crystals as small as 20 nm using solvent evaporation, a low energy crystallization method. Once synthesized, the crystals were protected in a chemical environment that significantly enhanced the stability of nanocrystals to polymorphism and dissolution.

Hydrogels consist primarily of water (or other aqueous solvent) embedded in a cross-linked polymeric network that provides mechanical strength. Here, hydrogels were modified to incorporate micelles into the network to produce nano-domains within which a crystallizing substance would nucleate and grow. The micelles can vary in structure to alter the size of the crystallization domains and the chemical environment to crystallize a wide range of materials. In particular, the ability to control the crystal size of hydrophobic active pharmaceutical ingredients was demonstrated.

Figure 2:
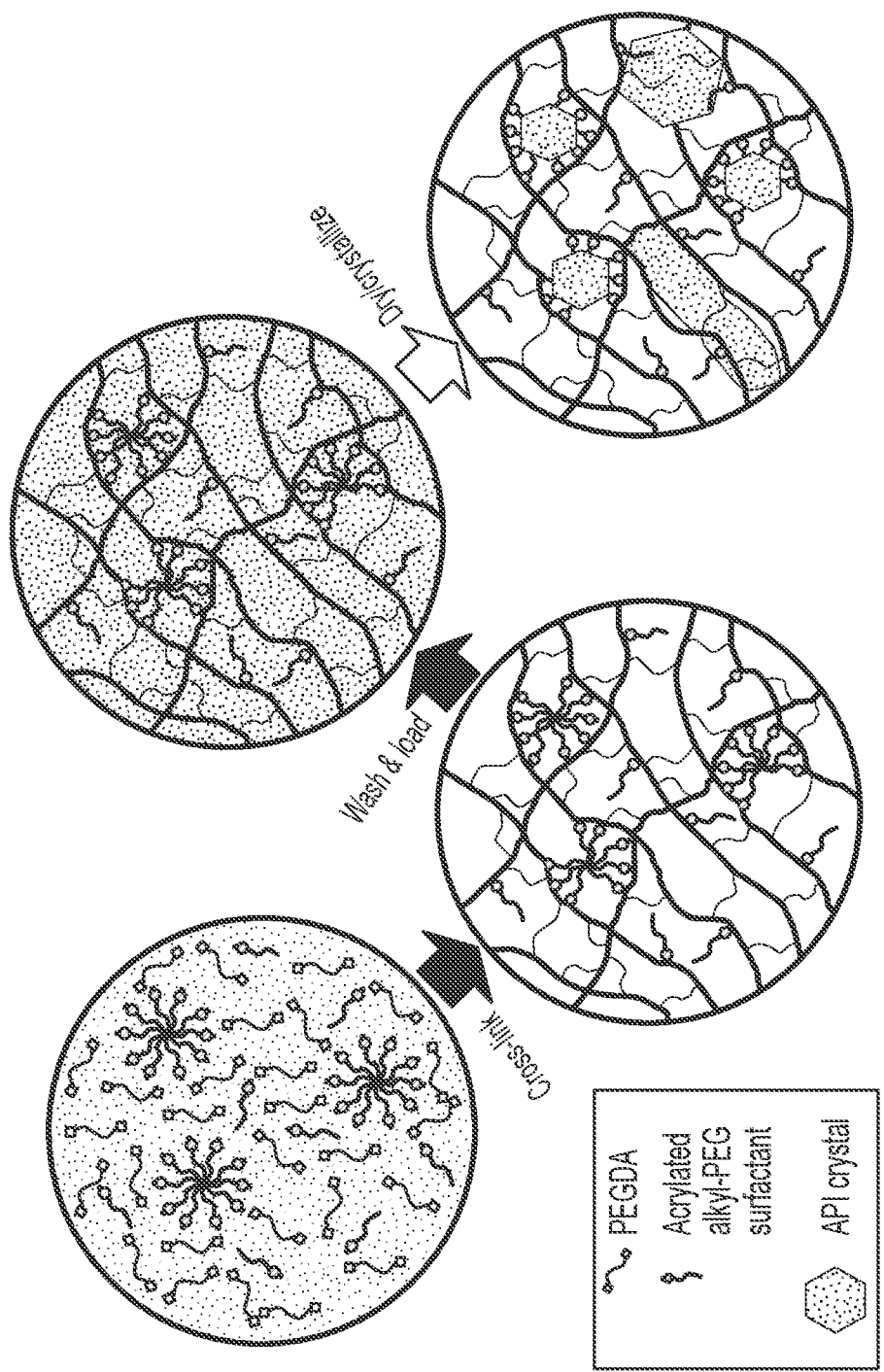
FIG. 2 shows a schematic of a process for producing crystals within a micelle-laden hydrogel matrix, according to one or more embodiments.

The matrix was composed of poly(ethylene glycol) diacrylate (PEGDA), which was cross-linked with a photoinitiator once exposed to UV light. In order to incorporate other chemical moieties into the matrix, they need only be modified to contain an acrylate bond so that it is chemically bound to the PEGDA network during the cross-linking reaction. A representative schematic is shown in FIG. 2. To synthesize micelle-laden hydrogels, PEGDA was first mixed with photoinitiator and surfactant molecules composed of a hydrophobic region of polyethylene and a hydrophilic region of poly(ethylene glycol) terminated with an acrylate group, which form spherical micelles in aqueous solution. This solution was exposed to UV light to cross-link the molecules and form the hydrogel network on which the micelles are chemically bound.

Once synthesized, these micelle laden hydrogels were then soaked in solvent with a crystallizing substance (solute). After loading the hydrogel with the crystallizing solution, solute crystal formation was induced by removing the solvent in an oven at an appropriate temperature for it to evaporate (a vacuum can be created to accelerate evaporation or reduce the temperature needed to evaporate). During evaporation, the solute concentration exceeded its solubility (supersaturates) and began to crystallize preferentially in the nano-domains formed by the micelles bound in the hydrogel matrix.

Figure 3A:
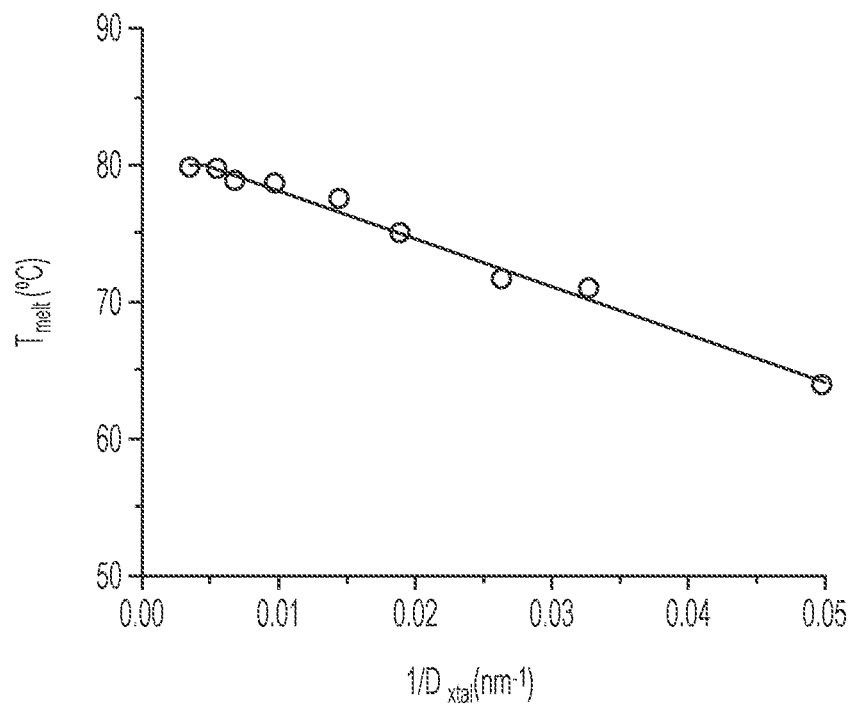
FIG. 3A shows a correlation between the melting temperature measure by DSC and the inverse of the effective size of fenofibrate (FEN) crystals fit with a correlation curve, according to one or more embodiments.
Figure 3B:
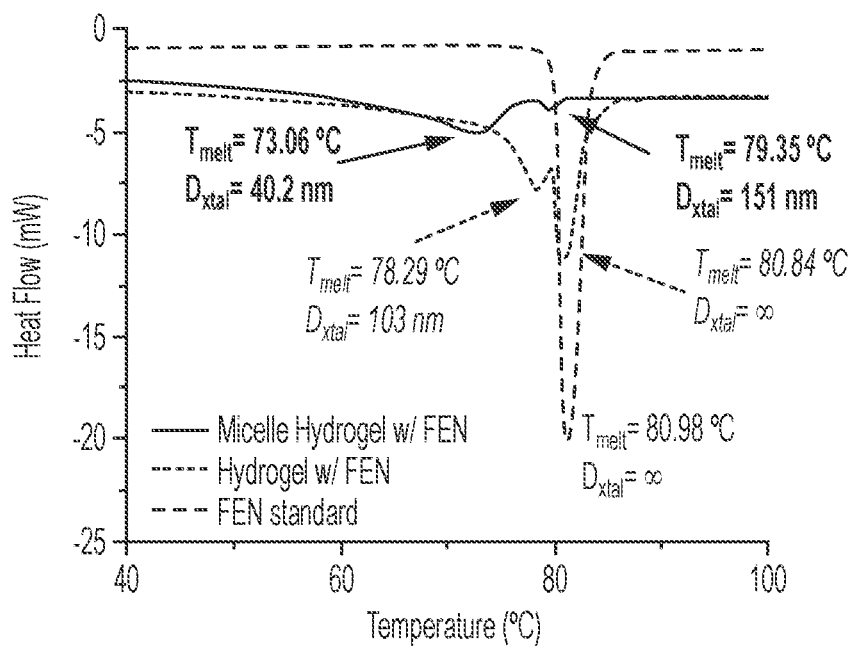
FIG. 3B shows a SDC thermograph of fenofibrate as bulk crystals (FEN standard), in a hydrogel matrix, and in a micelle-laden hydrogel, according to one or more embodiments.
Figure 4:
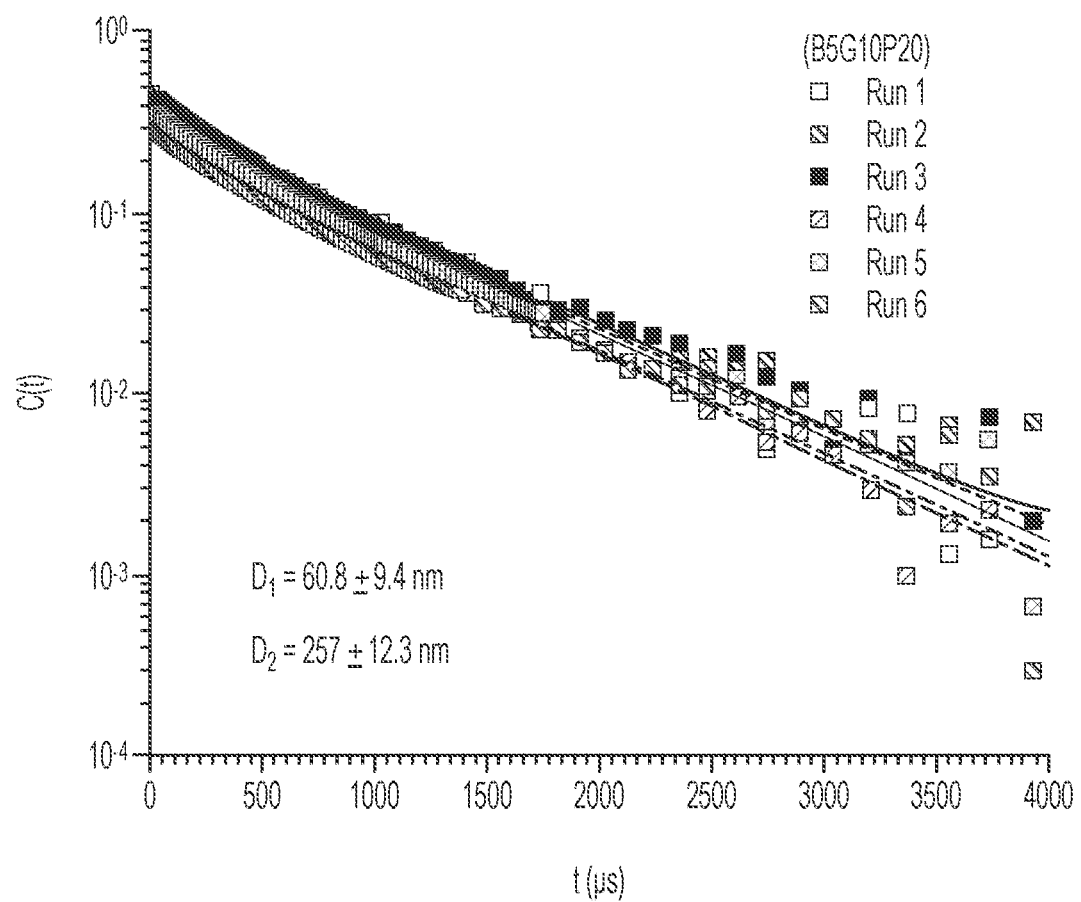
FIG. 4 shows a graph indicating DLS experiments of six different samples of decomposed micelle-laden hydrogels indicating that a bimodal distribution of crystal sizes are released from the nano-domains of about 61 nm and 257 nm, which is in agreement with DSC results.

The process was tested using a commercially available surfactant, poly(ethylene glycol) behenyl ether methacrylate (BPEGA), with a micelle size of 13 nm. Hydrogels were fanned with a mixture of PEGDA and BPEGA, washed to remove unreacted monomers, then loaded with fenofibrate, a model hydrophobic drug, suspended in ethyl acetate. After drying, the fenofibrate was found to have formed crystals of 40-60 nm, as determined from using differential scanning calorimetry (DSC), shown in FIGS. 3A and 3B, and dynamic light scattering (DLS), shown in FIG. 4. The crystals were slightly larger than the original micelle size, which was expected due to the low concentration of BPEGA surfactant and that the micelles expand after bonding to the cross-linked network. However, the local hydrophobic domain formed by the micelles produced a heterogeneous crystallization site to preferentially form nanocrystals embedded in the hydrogel matrix.

Non-Limiting Example 2

Example 2 describes further experimentation, embodiments, and non-limiting theories regarding the mechanisms and parameters guiding hydrogel and crystal formation. The materials and parameter values described in Example 2 are non-limiting and by way of example, only.

Crystallization of active pharmaceutical ingredients is an important processing step of manufacturing drug products. In particular, the crystal polymorph and size strongly influence the release and stability. While significant progress has been made in controlling these parameters, many processing techniques require high energy input and/or are unable to produce crystals in the nanoscale regime. To accommodate both of these conditions, hydrogel material was developed that serves as a template for nanocrystal formation through solution processing. These templates contain micelle structures ligated onto a hydrogel matrix. The micelle size, which is determined by the chemistry of the surfactant, dictates the size of the crystal. Therefore, nanocrystals can be produced in high yield with precisely controlled sizes ranging from 5 nm to 50 nm. Additionally, these hydrogels can serve as a delivery vehicle for enhanced uptake of hydrophobic drugs, as they simultaneously release drug with surfactant that increases the solubility in aqueous environments.

As a result of high-throughput methodologies for drug discovery, a significant portion of new drug substances are hydrophobic in nature. Hydrophobic active pharmaceutical ingredients (APIs) constitute roughly 40% of all small molecules that are commercially available or under development in pipelines. While hydrophobic APIs have received significant attention for their therapeutic activity, the limited solubility of these materials in aqueous environments limits their effectiveness as drug products. In particular, these drugs tend to have slow release rates and poor uptake. The size of crystals generated using top down approaches is limited to roughly 200-300 nm.

A promising solution to enhancing hydrophobic API solubility is the formulation of drug substances into nanocrystals. Manufacturing techniques to produce nanocrystalline API include ball mill rolling, spray drying, and emulsification. With regard to nanocrystalline APIs, a significant challenge exists to formulate drug products with an optimal combination of high drug loading, long-term stability, and fast release.

Hydrogels provide a platform for both synthesis and delivery of hydrophobic APIs by integrating ligands of hydrophobic chemistry into the matrix. Not only do hydrogels offer a mechanically stable environment for handling and processing, they do so will very small material quantity and porous microstructures to expedite mass transport.

Figure 5:
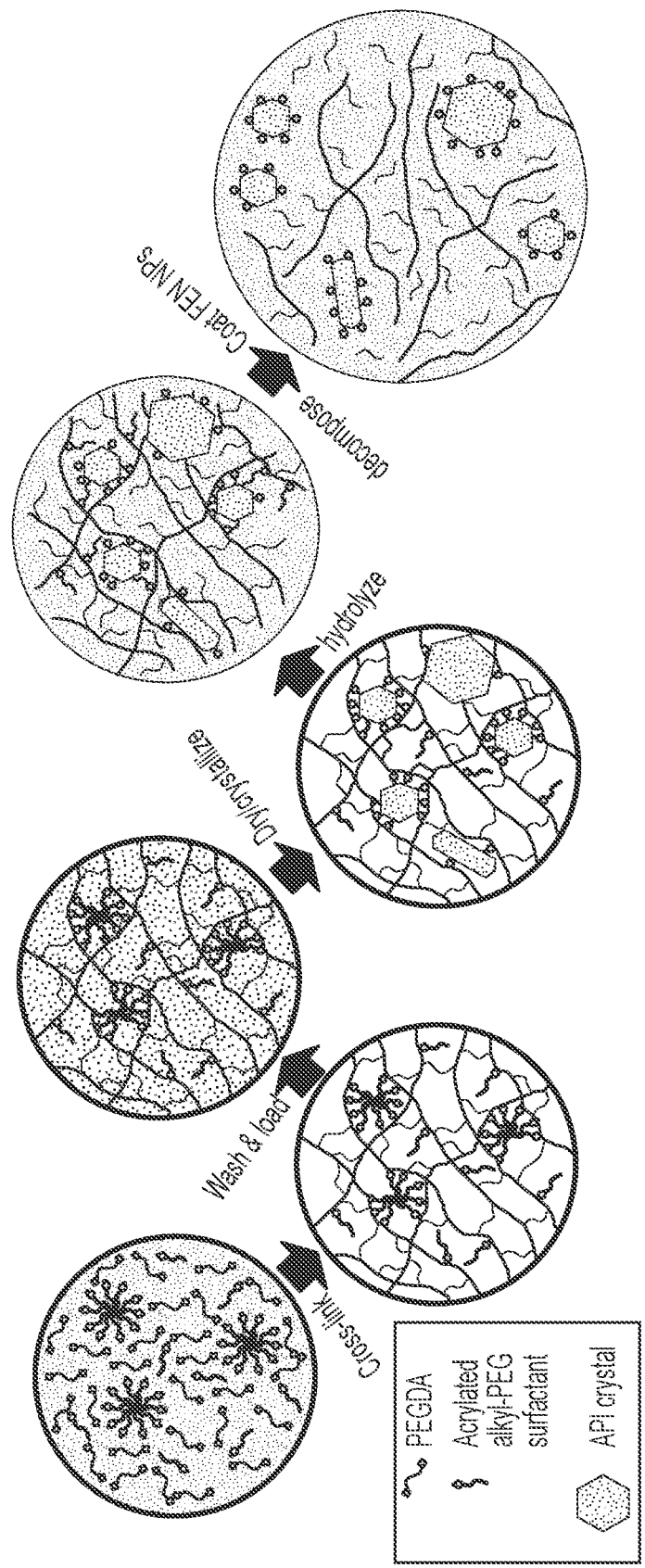
FIG. 5 shows a schematic of the micelle-laden hydrogel synthesis, followed by loading and crystallization of a hydrophobic API and finally re-hydration and release of stable nanocrystals of hydrophobic API, according to one or more embodiments.

The internalization of nanocrystals within a hydrogel helps enhance the stability of the nanocrystal by preventing coalescence. However, the crystal size is limited by the physical volume consumed by the organic solvent used during the synthesis process. Therefore, a minimalistic hydrophobic framework would include only surfactant (without solvent), which spontaneously forms micelles above the critical micelle concentration (CMC). FIG. 5 provides a schematic of how micelles can serve as a crystallization domain within hydrogels for the controlled synthesis and release of hydrophobic APIs. The scheme is based on the ability of the internal micelle space to serve as a hydrophobic domain to facilitate and control API crystallization. The organic medium containing hydrophobic API can be introduced post-synthesis of the hydrogel to initiate crystallization. In this form, the hydrogel stabilizes the nanocrystals from coalescence and degradation. When ingested, the hydrogel is then hydrolyzed, releasing both the API and surfactant simultaneously, aiding in the solubilization of the poorly water soluble drug and enhancing the release kinetics.

Experiments were performed to create and test hydrogels for crystal formation. Fenofibrate (FEN) was used as a standard hydrophobic API for its availability and extensive prior study. In particular, recent work has quantified the relationship between crystalline FEN melting point and crystal size by using porous glass beads with varying pore sizes.

Figure 6A:
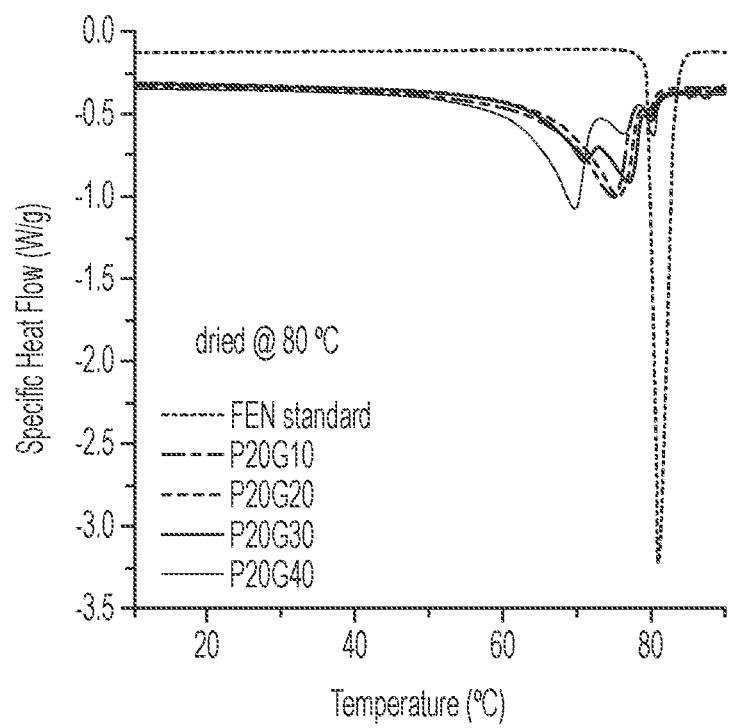
FIG. 6A shows a DSC thermogram showing specific heat flow for hydrogels with 20% PEGDA and varying volume percent of PEG porogen from 10% to 40% compared with a crystalline fenofibrate standard, according to one or more embodiments.

The significant void space of the matrix scaffold created domains within which crystallization could take place. Therefore, the PEGDA matrices that will later serve as the scaffold for acrylated micelles could themselves produce crystals with sizes dictated by the mesh size. Although the presence of surfactant, even not in micellar form, will alter crystallization in the mesh, quantifying the relationship between the matrix composition and crystal size set the foundation for identifying the effect of micellar domains. FIG. 6A shows a characteristic set of DSC thermograms of plain PEGDA hydrogels loaded with FEN compared with a bulk crystal standard. In all cases, the peaks shifted to smaller temperatures relative to the bulk sample, indicative of crystal sizes below about 500 nm. As the mesh size increased with larger contents of PEG porogen, multiple peaks appeared as a result of a polydisperse distribution of crystal sizes. Interestingly, the most significant species (i.e., the largest peak) became the smallest crystal size (roughly 30 nm in diameter) when the mesh was largest (20% PEGDA, 40% PEG: P20G40).

Figure 6B:
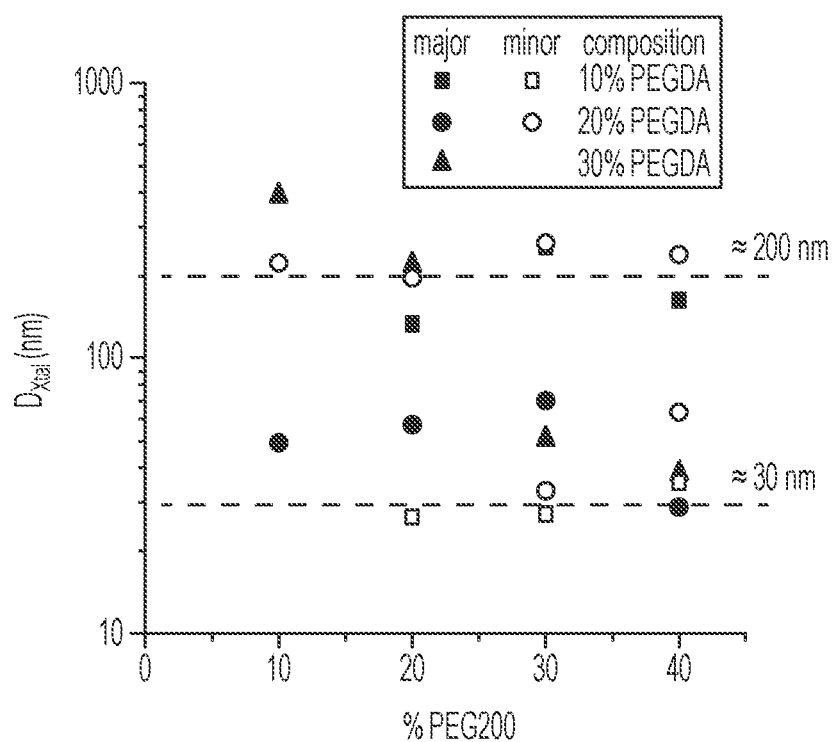
FIG. 6B shows a graph of crystal sizes determined by the temperature of the peak positions in DSC thermograms are compiled as a function of PEGDA and PEG porogen content of the hydrogels, according to one or more embodiments.

The results of all hydrogel compositions studied are compiled in FIG. 6b. The largest (major) peak(s) at each condition is (are) shown as filled symbol(s) and all other smaller (minor) peaks are shown as open symbols. At smallest PEGDA content (10% by volume), almost the entire population of crystals present were roughly 200 nm in size. While this was the largest crystal size found to form in PEGDA matrices, these are smaller than any other reported API crystals encapsulated in a hydrogel. As the PEGDA content was increased to 20% by volume, the predominant crystal size was shifted to roughly 30-50 nm, depending on the exact composition. At the highest PEGDA content studied (30% by volume), the peaks became much weaker, indicating a limitation to loading hydrophobic API. Interestingly, the sample with the smallest mesh size (30% PEGDA, 10% PEG) only showed signs of nearly macroscopic crystal formation. Yet when the PEG content was increased to 30% and 40% by volume, peaks indicating the formation of crystals on the order of 30-50 nm reappear.

The extensive and representative range of hydrogel compositions explored here indicates that PEGDA-based matrices can facilitate the formation of stable hydrophobic API nanocrystals. However, integrating micelles into these hydrogels further enhanced the loading of hydrophobic APIs and the formation of even smaller crystals. In the presence of surfactant, the hydrogel matrix facilitated crystal formation both directly and indirectly by supporting micellar domains. The matrix also indirectly influenced the hydrophobic domain size of the micelles if there was a size mismatch between the mesh and micelle diameter. If a micelle was larger than the mesh, then the internal domain sometimes became constricted or became destabilized. Alternatively, a mesh much larger than a micelle sometimes pulled individual surfactant molecules too far apart to maintain a cohesive hydrophobic domain.

TABLE 1

Summary of chemical properties of the surfactants used in this study, including the HLB value and chemical composition of the original surfactants and hydrodynamic diameter before ($D_h$) and after ($aD_h$) the acrylation reaction.

| surfactant | $M_w$ | HLB | # C/PPO | # PEO | $D_h$ (nm) | $\sigma_D$ (nm) | $aD_h$ (nm) | $\sigma_D$ (nm) |
|---|---|---|---|---|---|---|---|---|
| L10 | 627 | 13.6 | 12 | 10 | 8.43 | 0.5 | 10.5 | 0.3 |
| C10 | 683 | 12.9 | 16 | 10 | | | 12.6 | 0.8 |
| L23 | 1268 | 16.9 | 12 | 23 | 8.6 | 0.2 | 8.68 | 0.1 |
| C20 | 1124 | 15.7 | 16 | 20 | 10.1 | 0.1 | 10.2 | 0.1 |
| S20 | 1152 | 15.3 | 18 | 20 | 11.2 | 0.4 | 16 | 0.4 |
| B25 | 1496 | 17.3 | 22 | 25 | — | — | 12.8 | 0.1 |
| S100 | 4738 | 18.8 | 18 | 100 | 24.9 | 1.3 | 26.1 | 0.8 |
| F68 | 8400 | >24 | 30 | 80 | 7.07 | 0.2 | 12.5 | 0.4 |
| F127 | 12700 | 22 | 70 | 106 | 8.86 | 0.9 | 9.42 | 0.4 |

In order to explore the effect of surfactant properties on nanocrystal formation, a range of alkyl ethoxy and pluronic surfactants were integrated into hydrogel matrices. Table 1 outlines the surfactants studied, which vary in the length of the hydrophobic and hydrophilic units. The alpha numeric names refer first to the alkyl chain (L=lauryl, C=cetyl, S=stearyl, and B=behenyl) and second to the PEG length in number of monomeric units. The two pluronic triblock surfactants studied are F68 and F127, which contain a polypropylene glycol (PPG) hydrophobic region rather than an alkyl chain. Due the folding necessary for pluronics to form micelles, the "effective" length of their hydrophobic region is half that of the PPG segment listed in Table 1. The surfactants are organized into three sub-sections distinguished by the size of the PEG region, which correspond to roughly 10, 20, and 100 PEG units. Thus, the influence of the size of the PEG segment and hydrophobic core of the micelle could be independently studied.

Figure 7A:
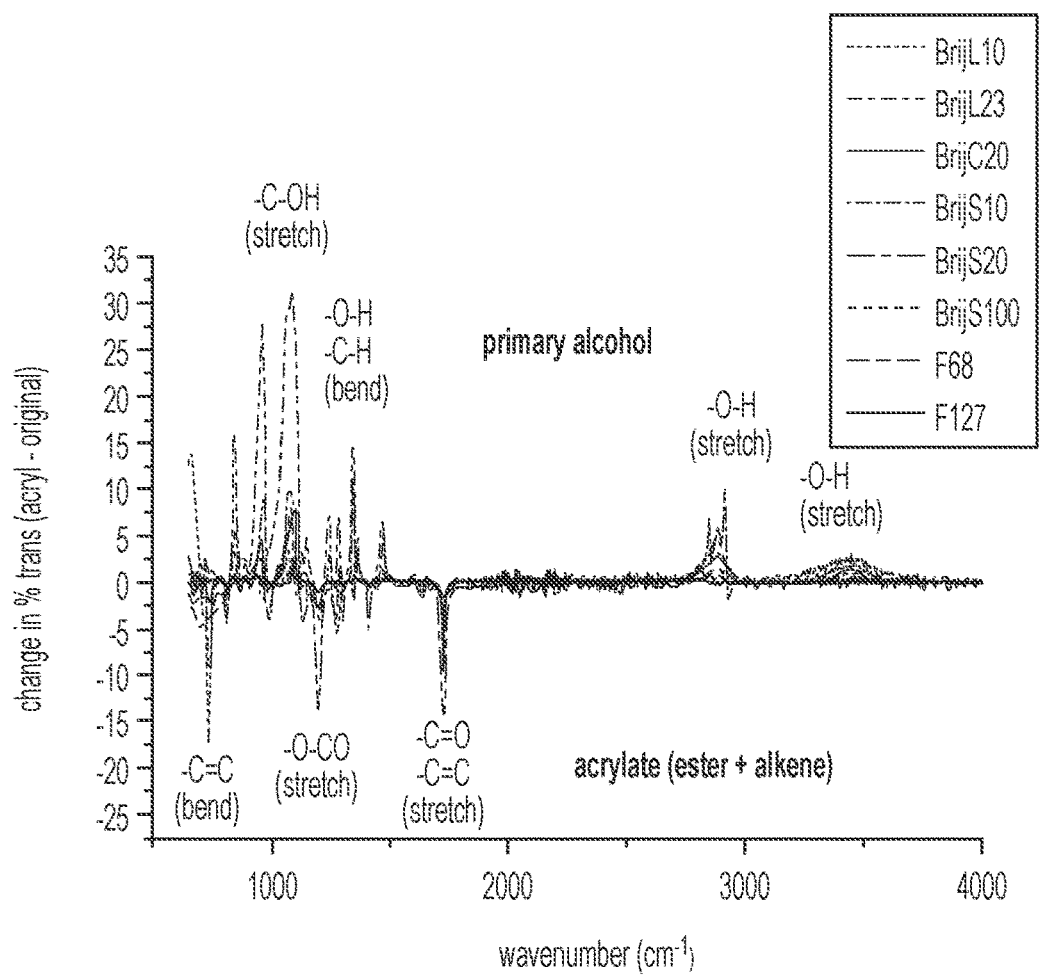
FIG. 7A shows a graph indicating change in transmission using FTIR after the addition of an acrylate group onto Brij and pluronic surfactants, according to one or more embodiments.
Figure 7B:
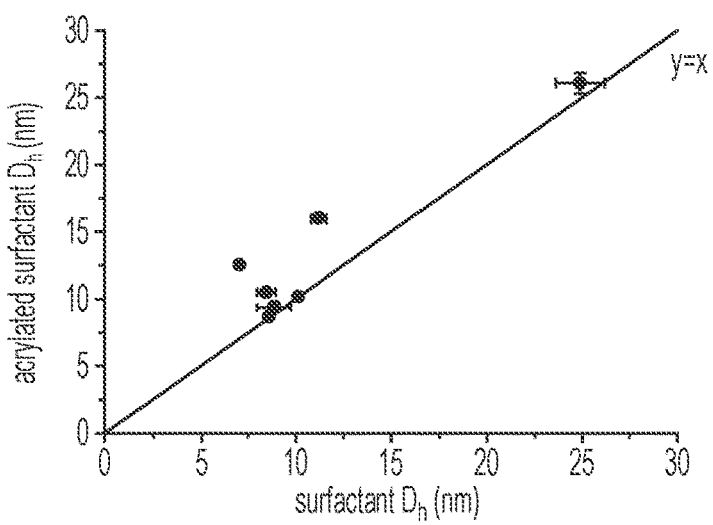
FIG. 7B shows a graph indicating hydrodynamic diameters determined by DLS of each surfactant are compared directly, demonstrating little to no change in the micelle size after the addition reaction, according to one or more embodiments.

Integrating micelle templated hydrophobic domains into hydrogel matrices was facilitated by the surfactants being capable of chemical bonding into the polymer backbone. To become reactive and compatible with PEGDA based hydrogels, an acrylate functional group was attached to the end of the PEG segment (see the Methods and Materials sections for details) of each surfactant except B25, which was purchased commercially in the acrylated form. To confirm the surfactants remain water soluble and form micelles after acquiring an acrylate group, low concentration solutions were tested by FTIR and DLS. FIG. 7A shows the change in FTIR transmission after acrylate group addition. The negative peaks indicated the addition of new vinyl and carbonyl bonds and the positive peaks confirmed the removal of the primary alcohol group. Hydrodynamic diameters determined by DLS before ($D_h$) and after ($aD_h$) the reaction are provided in Table 1 and compared visually in FIG. 7B. In most cases, the addition of an acrylate group had no effect on the micelle size. For two surfactants (S20 and F68) the deviation in $D_h$ was noticeable, but the increase in apparent hydrodynamic diameter after the reaction was likely the result of enhanced association between micelles rather than the formation of larger micelles.

An optimal micelle laden hydrogel formulation would yield high loading of API nanocrystals with minimal surfactant content. The critical micelle concentration of the surfactants used here were all on the order of 10 μM, providing a small barrier to the formation of micelles and therefore of nanoscale hydrophobic domains. However, given that pores within the hydrogel mesh serve as nucleation centers, a critical density of micelle domains facilitated driving crystallization to preferentially occur within these hydrophobic domains and yield an appreciable content of nanocrystals. In the other extreme, at high surfactant concentrations, spherical micelles may transition to larger lengthscale structures, such as vesicles, sheets, or worm like micelles, or self-associate into ordered cubic phases causing gelation (causing solution processing to be more difficult). As a result, a range of concentrations was studied for a subset of surfactants at a set matrix composition to identify these possible outcomes.

Figure 8A:
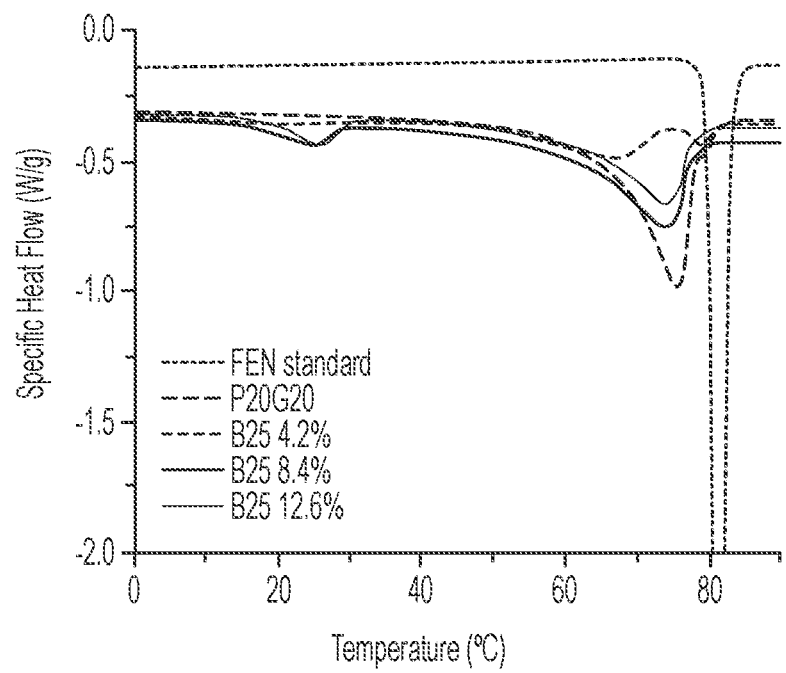
FIG. 8A shows a graph indicating DSC thermograms at three concentrations (4.2%, 8.4%, and 12.6% w/v) for the surfactant B25 compared to a bulk FEN standard and the P20G20 matrix alone, according to one or more embodiments.
Figure 8B:
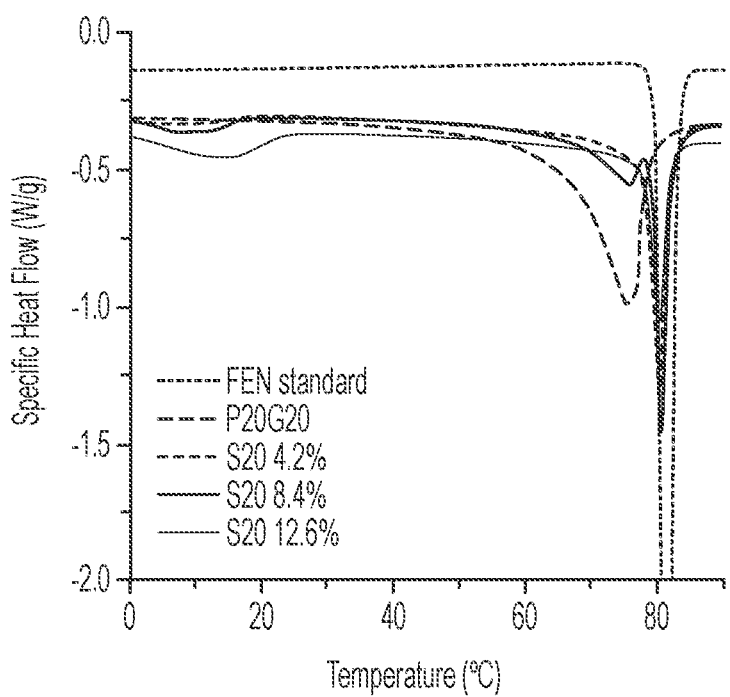
FIG. 8B shows a graph indicating DSC thermograms at three concentrations (4.2%, 8.4?, and 12.6% w/v) for the surfactant S20 compared to a bulk FEN standard and the P20G20 matrix alone, according to one or more embodiments.
Figure 8C:
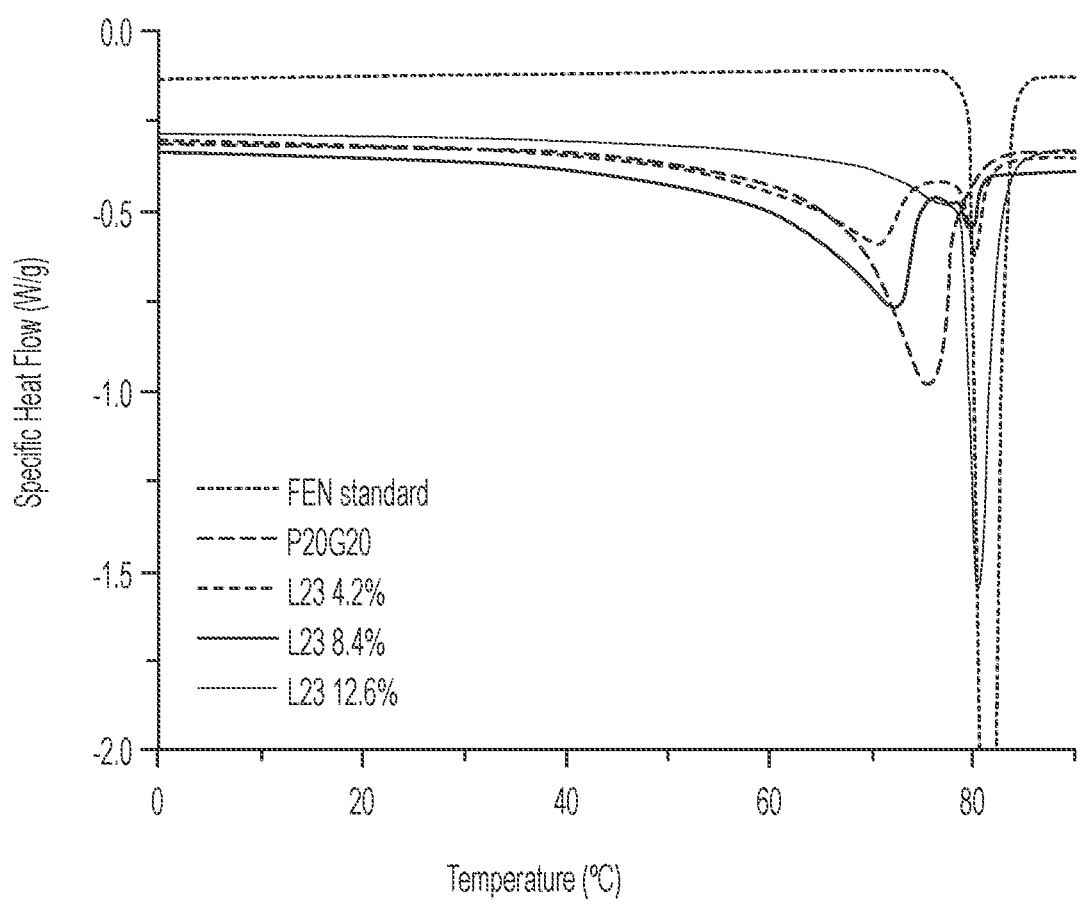
FIG. 8C shows a graph indicating DSC thermograms at three concentrations (4.2%, 8.4%, and 12.6% w/v) for the surfactant L23 compared to a bulk FEN standard and the P20G20 matrix alone, according to one or more embodiments.

The effect of surfactant chemical structure is highlighted in FIG. 8 by comparing three surfactants and three concentrations in a hydrogel matrix composed of 20% PEGDA and 20% PEG (P20G20). At the lowest concentration studied, none of the surfactants produce a peak in the thermogram well below that of the "pure" matrix. This is illustrated in FIG. 8A. In fact, the acrylated S20 surfactant actually induces the formation of larger crystals compared to when it was not present. This might be the result of enhanced association between fenofibrate and monomers randomly integrated into the mesh backbone. However, as the concentration was increased, small and broad peaks began to form between 15° C. and 25° C. in the thermograms of B25 and S20 laden hydrogels. This is illustrated in FIG. 8B. Simultaneously, the peaks at higher temperatures became smaller, indicating an overall shift in the crystal size distribution towards that of smaller nanocrystals. Surfactant L23, with a 12 carbon alkyl chain compared to 18 and 22 carbons in the S20 and B25 alkyl chains, respectively, does not show any signs of sub 100 nm nanocrystal formation. The lack of small nanocrystals suggests that the internal hydrophobic domain size produced by this alkyl chain length was too small to support the formation of API crystals. Similar to surfactant S20, L23 produced nearly bulk size crystals at the highest concentration studied. This is illustrated in FIG. 8C. It is uncertain whether this was a result of enhanced wetting of the mesh by fenofibrate given the presence of hydrophobic ligands or if large scale micellar structures were forming at elevated concentrations.

Figure 9A:
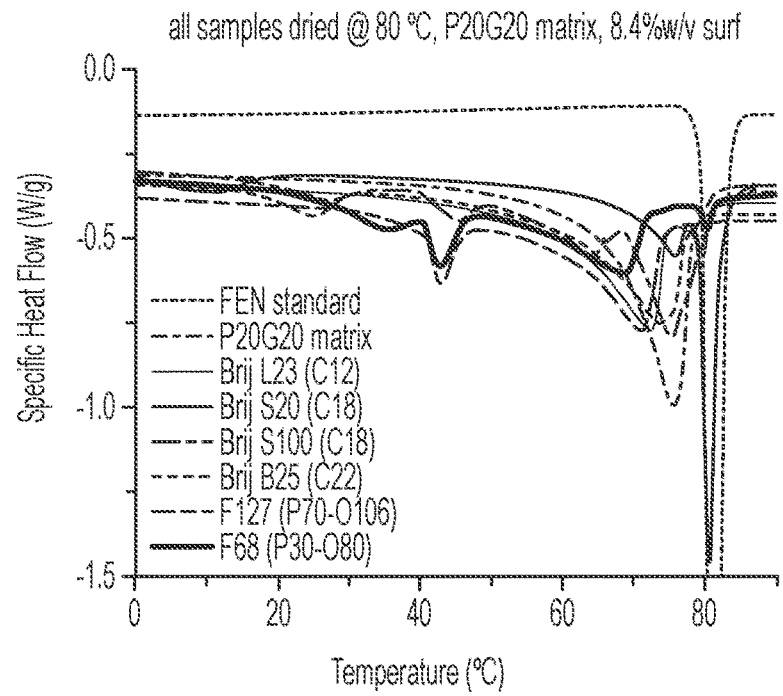
FIG. 9A shows a graph indicating DSC thermograms of all surfactants listed in Table 1 embedded in P20G20 hydrogel matrixes relative to a bulk FEN standard and the pure matrix, according to one or more embodiments.
Figure 9B:
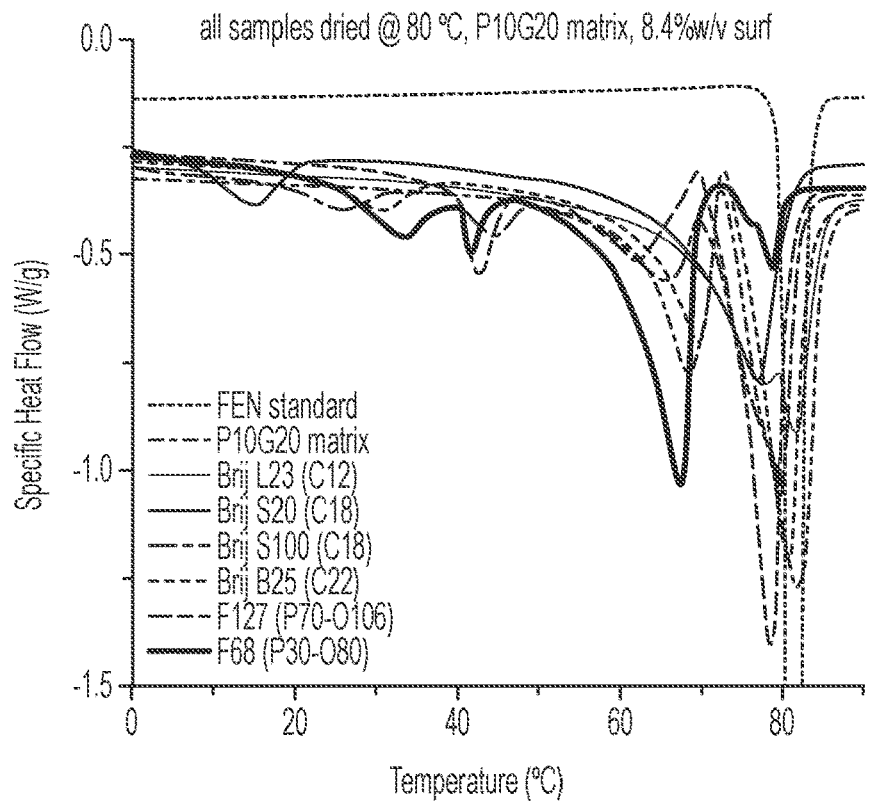
FIG. 9B shows a graph indicating DSC thermograms of all surfactants listed in Table 1 embedded in P10G20 hydrogel matrix relative to a bulk FEN standard and the pure matrix, according to one or more embodiments.

To identify the chemical requirements for micelles to template the formation of sub 100 nm crystals, a wide range of surfactants are studied using three different matrix compositions. Each of the surfactants listed in Table 1 were formulated at a concentration of 8.4% w/v with 10%, 20%, and 30% PEGDA with 20% PEG as a porogen. This surfactant concentration is the middle condition shown in FIG. 8B, which provides a balance of mitigating bulk-size crystal formation and promoting small nanocrystal formation. The variation in matrix composition provided a range of mesh sizes to quantify the influence of the hydrogel scaffold on micelle templating. The resulting DSC thermograms are shown in FIG. 9 for all matrix and surfactant combinations. For all three matrix compositions, all surfactants except L10 and L23 and C10 and C20 were able to form sub 10 nm crystals. Under all conditions Where micelles appear to template nanocrystal formation, peaks still appeared at higher temperatures comparable to those found without the presence of surfactant, but at a smaller magnitude.

TABLE 2

Summary of crystal sizes extracted from each of the peaks below 80° C. in the thermograms shown in FIG. 9. Table 2 displays the type of surfactant, the temperature of the peak (T (° C.)), the weighted average diameter of the crystal (D (nm)), and the mass fraction of crystals that are that diameter (X (D)).

| surfactant | T (° C.) | D (nm) | X(D) |
|---|---|---|---|
| P20G20 | | | |
| L23 | 67.9 | 25.1 | 0.934 |
| L23 | 77.4 | 81.5 | 0.030 |
| S20 | 8.0 | 4.7 | 0.501 |
| S20 | 71.8 | 35.0 | 0.260 |
| S100 | 25.9 | 6.2 | 0.169 |
| S100 | 44.8 | 9.4 | 0.074 |
| S100 | 62.4 | 18.0 | 0.304 |
| B25 | 23.6 | 5.9 | 0.258 |
| B25 | 70.5 | 30.9 | 0.742 |
| F127 | 42.2 | 8.8 | 0.311 |
| F127 | 67.8 | 24.9 | 0.689 |
| F68 | 33.8 | 7.2 | 0.326 |
| F68 | 44.0 | 9.2 | 0.250 |
| F68 | 64.0 | 19.6 | 0.415 |
| P10G20 | | | |
| L23 | 73.64825 | 43.21311 | 0.769526 |
| S20 | 13.43103 | 5.056383 | 0.398763 |
| S100 | 25.22653 | 6.113848 | 0.157286 |
| S100 | 44.05576 | 9.177786 | 0.09495 |
| S100 | 63.488 | 19.00937 | 0.259943 |
| B25 | 29.72015 | 6.643119 | 0.169097 |
| B25 | 64.88149 | 20.59116 | 0.466006 |
| F127 | 42.4963 | 8.812037 | 0.18683 |
| F127 | 61.22564 | 16.90148 | 0.270483 |
| F68 | 31.97433 | 6.944703 | 0.272263 |
| F68 | 42.01518 | 8.70501 | 0.068864 |
| F68 | 64.05022 | 19.61738 | 0.603896 |
| F68 | 79.05098 | 133.8095 | 0.055031 |

Figure 11A:
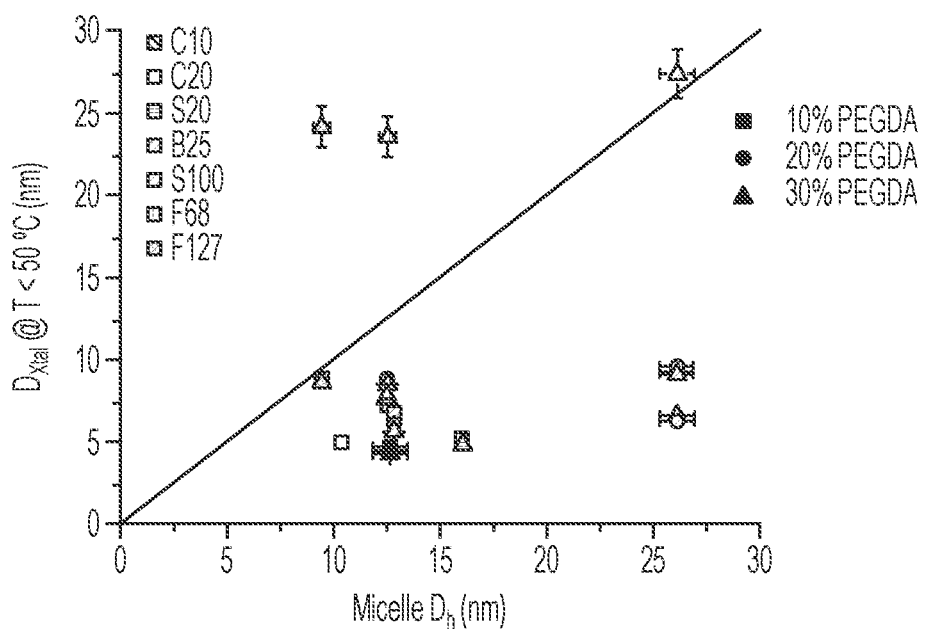
FIG. 11A shows a graph indicating a comparison of micelle hydrodynamic diameter, measured by DLS, with the smallest crystal sizes extracted from DSC thermograms ($T_{melt} < 50°$ C.) (the y=x line is shown as a guide to the eye), according to one or more embodiments.
Figure 11B:
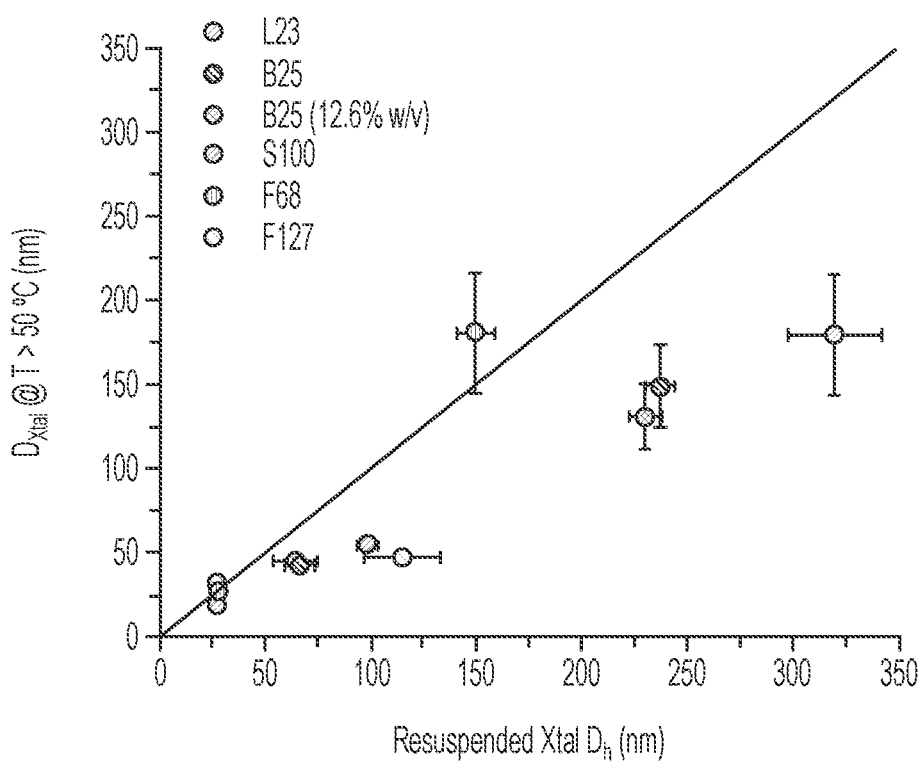
FIG. 11B shows a graph indicating a comparison of the effective hydrodynamic diameter after decomposing FEN loaded hydrogels with the crystal sizes extracted from DSC thermograms at high temperatures (T>50° C.) (the y=x line is shown as a guide to the eye), according to one or more embodiments.

Crystal sizes appear to correlate roughly with the hydrodynamic diameter of the micelle prior to integration into a hydrogel. Table. 2 shows a summary of the crystal sizes extracted from each of the peaks below 80° C. in the thermograms shown in FIG. 9. FIG. 11A shows a graph indicating a comparison of micelle hydrodynamic diameter, measured by DLS, with the smallest crystal sizes extracted from DSC thermograms ($T_{melt}$<50° C.) (the y=x line is shown as a guide to the eye). Crystal sizes close to those produced without surfactant present are not included to highlight the effect of micelles. Under all conditions, the hydrodynamic diameter of the micelles set an upper limit for nanocrystal size. That the final crystal size was typically smaller than the micelle reflects the fact that the internal hydrophobic corona was only a fraction of the total volume of the micelle. Further, the hydrogel matrix composition did not appear to influence the size of crystals formed within micelles if they were capable of inducing crystallization. The primary influence of matrix composition was on the size of crystals on the order of 50 nm to 200 nm. Depending on the combination of surfactant and mesh, the size and population of these intermediate nanocrystals will shift slightly. Additionally, FIG. 11B shows a graph indicating a comparison of the effective hydrodynamic diameter after decomposing FEN loaded hydrogels (see below), with the crystal sizes extracted from DSC thermograms at high temperatures (T>50 CC) (the y=x line is shown as a guide to the eye).

In addition to the formation of 10 nm crystals by micelles ligated into hydrogels, the surfactant also served as a means to increase the loading of drug within the matrix and enhance the solubility during delivery. Loading is quantified by UV-vis spectroscopy with a calibration curve produced by solubilizing fenofibrate in aqueous solution using sodium dodecyl sulfate, SDS. The hydrogels loaded with hydrophobic API were suspended in a solution of 0.6 M SDS in order to extract the entire content of loaded drug.

Figure 10:
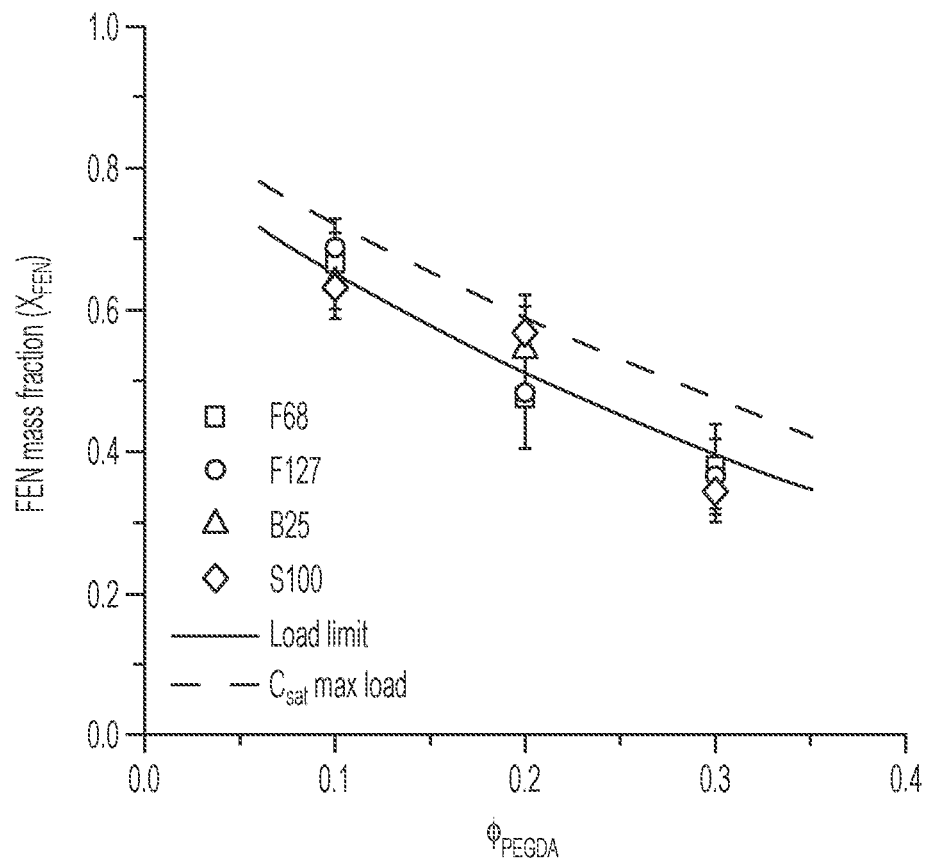
FIG. 10 shows a graph in which the fraction of FEN loaded in hydrogels as measured by the fraction of mass lost using TGA is plotted as a function of PEGDA content. All samples were loaded in a solution of 450 mg/mL fenofibrate in ethyl acetate with an upper limit of loading efficiency represented by the solid line. The maximum possible loading with a saturated solution (620 mg/mL) is shown by the dashed line, according to one or more embodiments.

The drug loading is also measured by thermal gravimetric analysis (TGA) for four different surfactants. FIG. 10 shows a graph in which the fraction of FEN loaded in hydrogels as measured by the fraction of mass lost using TGA is plotted as a function of PEGDA content. All samples were loaded in a solution of 450 mg/mL fenofibrate in ethyl acetate with an upper limit of loading efficiency represented by the solid line. The maximum possible loading with a saturated solution (620 mg/mL) is shown by the dashed line. Additionally, FIG. 13 shows the fraction of mass remaining as measured by TGA plotted as a function of temperature for hydrogels with varying amounts of PEGDA comprising the matrix. All hydrogels shown here are laden with F127 micelles and loaded with a solution of 450 mg/mL fenofibrate in ethyl acetate before drying.

Enhanced solubility during release was also tested by expedited decomposition. For this, the hydrogels are hydrolyzed in a 1.0 M sodium hydroxide solution. The release of both drug and surfactant yielded a suspension of stabilized crystals that would typically be impossible due to the poor solubility of fenofibrate in water. The crystal size was tested by DLS while the content of drug released without added SDS is quantified by UV-Vis. Without the presence of SDS to enhance the aqueous solubility of fenofibrate, the surfactant released from the hydrogels was capable of solubilizing a mass of fenofibrate equal to roughly 3% of the formulated and loaded hydrogel. This mass equated to roughly 10% of the total fenofibrate load within the hydrogels.

Under all conditions tested, two "large" nanocrystal peaks were present in DSC thermograms and yielded two decay modes in the DLS correlation function.

To conclude, the ability to integrate acrylated surfactants into PEGDA based hydrogel scaffolds to serve as domains for the crystallization of nanocrstalline hydrophobic APIs was demonstrated. The model hydrophobic drug, fenofibrate, was used for its available calibration curve comparing crystal size to melting temperature in order to identify the distribution of crystal sizes formed in micelle-laden hydrogels. Nanocrystals on the order of 50 nm to 200 nm were found to form in plain hydrogels without surfactant present, which was already an extensive reduction in crystal size compared to commonly used top-down micronization techniques. The addition of surfactant in the form of micelles provided hydrophobic domains that successfully templated the formation of nanocrystals smaller than 10 nm in size. An 18 carbon (stearyl) chain was found to be the minimum size of the hydrophobic segment of the surfactant to reliably induce crystallization of the hydrophobic API studied. Depending on the application, the composition of the hydrogel and surfactant can be tuned to produce a wide range of crystal size distributions. The loading of API in these micelle laden hydrogels can theoretically reach up to roughly 80% by mass, though the maximum loading reached here with fenofibrate was about 70%. Under all conditions, the presence of surfactant also stabilized nanocrystals of about 20 nm and larger when released from the hydrogel scaffold after decomposition. All smaller crystals appeared to agglomerate due to their inherent instability. Therefore, these micelle-laden hydrogels serve as an effective framework to synthesize nanocrystals of hydrophobic APIs and enhance their release and solubility during delivery.

All chemical constituents of hydrogel induced crystallization, including ethanol, ethyl acetate, fenofibrate [FEN], 3-hydroxypropylacetophenone [photoinitiator, PI], poly(ethylene glycol) [PEG], poly(ethylene glycol) diactylate [PEGDA], poly(ethylene glycol) behenyl ether acrylate [BPEGA] solution, were purchased from Sigma-Aldrich and used as received. Hydrogels were synthesized by first combining 5% by volume photoinitiator with varying volumes of PEG, PEGDA, acrylated surfactant, and DI water then pouring this pre-cursor solution into a PDMS mold and exposing to a UV lamp (365 nm, 1.3 W) for 10 min. Any excess PI, PEG, and unreacted acrylated components were removed by washing in ethanol three times.

Other acrylated surfactants were synthesized by acylation of commercially available PEG alkyl ether surfactants. The reaction components, including dichloromethane [DCM], acryloyl chloride, sodium bicarbonate, and all surfactants used (Brij L20 and Brij L100), were purchased from Sigma-Aldrich and used as received. The reaction procedure of prior studies was used, which were carried out at room temperature using an Erlenmeyer flask on a stir plate. The surfactant of choice was first solubilized in DCM under gentle stirring before adding a 20% molar excess of sodium bicarbonate. An identical molar excess quantity of acryloyl chloride was separately added to a small amount of DCM, which was then added dropwise to the surfactant mixture under gentle stirring. The reaction was carried out overnight (18-24 hrs). The mixture was filtered through a Buchner funnel to remove solids then the solvent was removed under vacuum at 30° C.

Figure 12A:
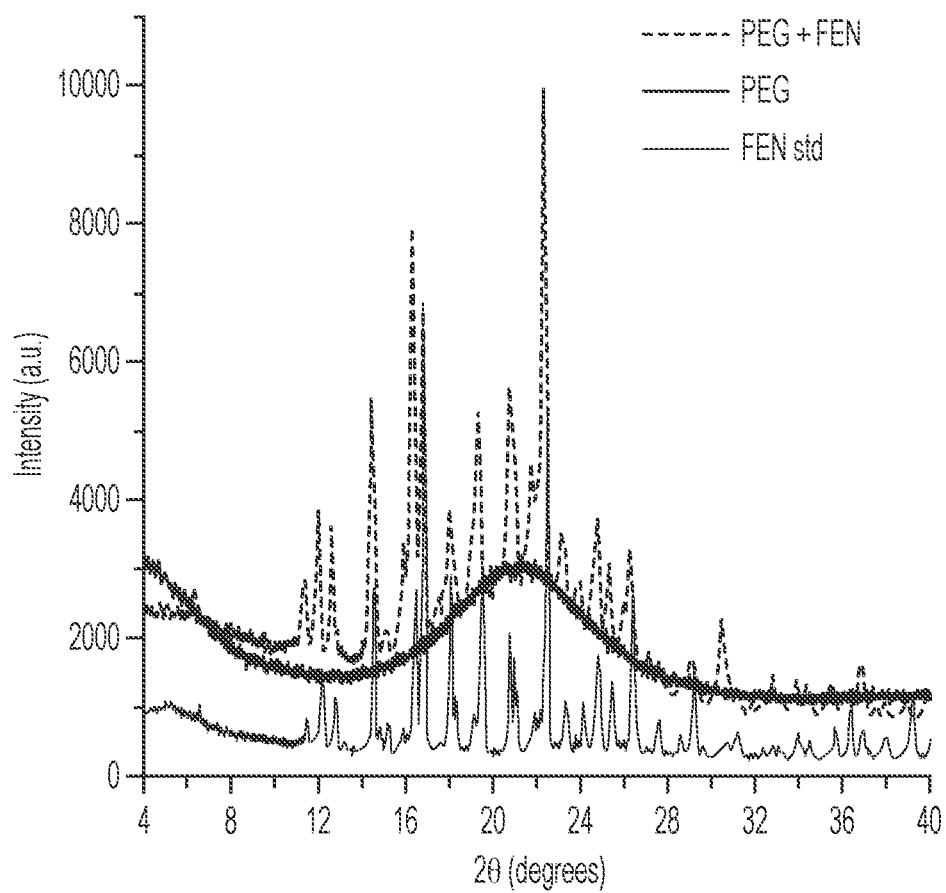
FIG. 12A shows XRD results demonstrating the integration of fenofibrate (FEN) crystals into PEGDA based matrices. The hydrogel (thick black line) shows only one broad peak corresponding to the disordered mesh while the FEN loaded hydrogel (dashed line) shows both features of the hydrogel and the peaks corresponding to a crystalline fenofibrate standard (thin black line), according to one or more embodiments.
Figure 12B:
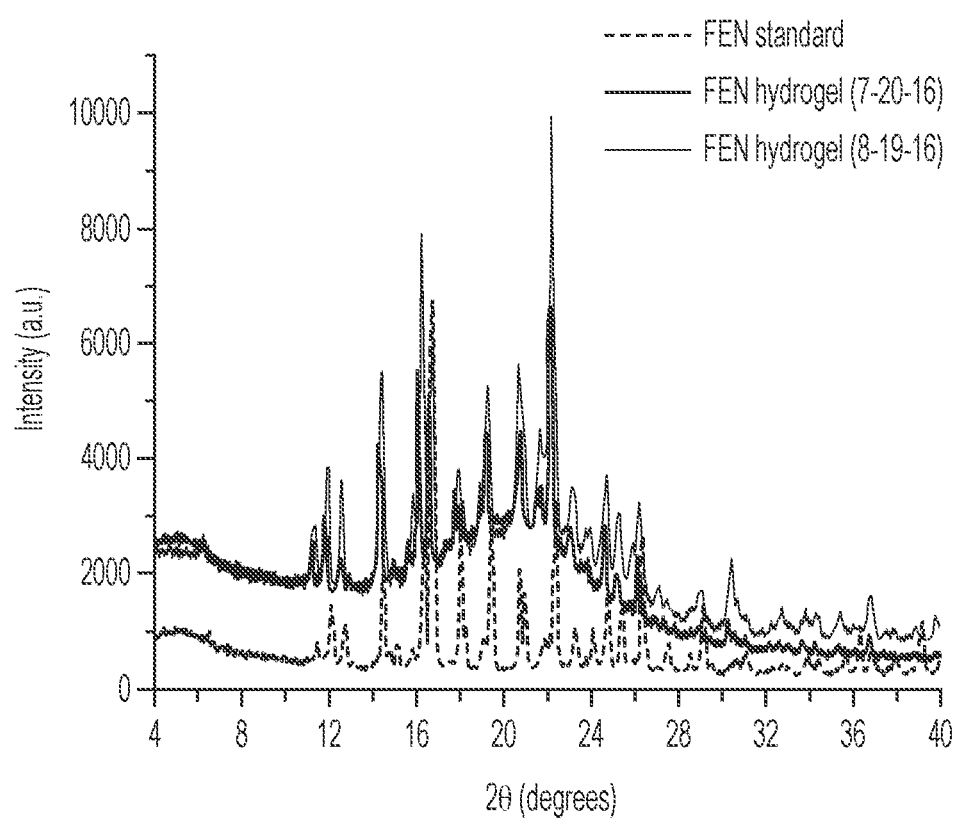
FIG. 12B shows XRD results demonstrating the stability of fenofibrate (FEN) crystals in PEGDA based matrices. The initially synthesized crystals in the FEN loaded hydrogel (thick black line) show both features of the hydrogel and the peaks corresponding to the crystalline fenofibrate standard (dashed line). The XRD spectrum of a sample from the same set of crystals, after being stored at room temperature and 40% relative humidity for 30 days, is shown as the thin line and displays shows the same features as the blue curve, according to one or more embodiments.

Crystallization was carried out by first soaking hydrogels in ethyl acetate, then removing supernatant and adding FEN loaded ethyl acetate. Hydrogels were allowed to soak in FEN solution for at least three hours before removing supernatant and drying the hydrogel in a vacuum at 80° C. overnight (18-24 hrs). The crystalline FEN within hydrogels was characterized by X-ray diffraction (XRD) and dynamic scanning calorimetry (DSC) to confirm the polymorph of the crystal and the crystal size, respectively. FIG. 12A shows XRD results demonstrating the integration of fenofibrate (FEN) crystals into PEGDA based matrices. The hydrogel (thick black line) shows only one broad peak corresponding to the disordered mesh while the FEN loaded hydrogel (dashed line) shows both features of the hydrogel and the peaks corresponding to a crystalline fenofibrate standard (thin black line). The substantial stability of the FEN crystals was demonstrated by comparing XRD patterns before and after the FEN loaded hydrogel was stored for a period of time. A nano-templated hydrogel loaded with nanocrystalline fenofibrate was stored in a (non-air-tight) petri dish under normal, but uncontrolled, lab conditions (roughly 22° C. and 40% relative humidity) for 30 days. FIG. 12B compares the XRD patterns of FEN-loaded nano-templated hydrogels before (Jul. 20, 2016) (thick black curve) and after (Aug. 19, 2016) (think black curve) storage, along with a standard XRD curve for bulk fenofibrate (dashed curve), demonstrating that the crystal structure (polymorph) is substantially unchanged over one month. XRD experiments were carried out on a PANalytical XPert Pro with a 4° aperture and 0.5° slit using a continuous scanning detector ranging from a 2θangle of 4° to 40° with a scan rate of 1°/min. DSC experiments were conducted on a TA Instruments Q2000 using aluminum pans and equilibrating at −20° C. before ramping temperature at a rate of 10° C./min to a maximum of 180° C.

Properties of FEN nanocrystals after re-suspending in aqueous media after crystallization were characterized by two different methods. First, the crystal size was measured using DLS after decomposition of the hydrogel matrix in 1 M sodium hydroxide solution. A small amount of hydrogel was allowed to sit in basic solution overnight at room temperature with gentle stirring. The solution was then left for an additional day without stirring to allow matrix residue to settle, leaving behind a clear suspension of nanocrystals. Second, the amount of FEN released was quantified using UV-Vis absorbance at a wavelength of 280 nm. A calibration curve was produced in aqueous solutions of 0.6 M SDS with FEN concentrations ranging from 1 µg/mL to 10 µg/mL.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A composition, comprising:
    a hydrogel, comprising:
    a cross-linked polymeric matrix comprising a cross-linked species and a cross-linking agent; and
    a plurality of micelles comprising poly(ethylene glycol) behenyl ether acrylate bonded to the cross-linked polymeric matrix,
    wherein the plurality of micelles comprises a hydrophobic crystal seeding material.

2. The composition of claim 1, wherein the hydrogel further comprises an aqueous solvent.

3. The composition of claim 1, wherein the cross-linked species is selected from the group consisting of poly(ethylene glycol) and its derivatives, cellulose and its derivatives, poly(propylene glycol) and its derivatives, polylactide and its derivatives, poly(glycolic acid) and its derivatives, poly(propylene fumarate) and its derivatives, polycaprolactone and its derivatives, polyhydroxybutyrate and its derivatives, polyacrylates and derivatives, poly(vinylpyrrolidone) and derivatives, and poly(ethylenimine) and its derivatives.

4. The composition of claim 1, wherein the cross-linked species comprises PEGDA.

5. The composition of claim 1, wherein the cross-linking agent comprises a photoinitiator.

6. The composition of claim 5, wherein the photoinitiator is selected from the group consisting of alkylphenones, acetophenones, benzoin ethers, acyl phosphine oxides, benzophenones.

7. The composition of claim 1, wherein the plurality of micelles comprise surfactant.

8. The composition of claim 7, wherein the surfactant is a non-ionic surfactant.

9. The composition of claim 8, wherein the non-ionic surfactant comprises a hydrophobic region and a hydrophilic region.

10. The composition of claim 1, wherein each of the plurality of micelles define a micelle core.

11. The composition of claim 10, wherein the micelle cores have an average diameter of from 5 nm to 50 nm.

12. The composition of claim 10, wherein the micelle cores define hydrophobic domains configured to facilitate crystallization of the hydrophobic crystal seeding material.

13. The composition of claim 12, further comprising the hydrophobic crystal seeding material positioned in the hydrophobic domains.

14. The composition of claim 13, wherein the hydrophobic crystal seeding material comprises an active pharmaceutical ingredient.

15. The composition of claim 14, wherein the active pharmaceutical ingredient is hydrophobic.

16. The composition of claim 12, further comprising substantially stable crystals positioned in the hydrophobic domains.

17. The composition of claim 16, wherein the stable crystals have an average diameter of from 5 nm to 200 nm.

* * * * *